US010196447B2

(12) United States Patent
Wu et al.

(10) Patent No.: US 10,196,447 B2
(45) Date of Patent: Feb. 5, 2019

(54) ANTI-VASCULAR ENDOTHELIAL GROWTH FACTOR RECEPTOR 2 (VEGFR2) ANTIBODY AND METHODS OF USE THEREOF FOR DETECTING VEGFR2 AND FOR INHIBITING TUMOR GROWTH, TUMOR ANGIOGENESIS AND/OR INDUCING CANCER CELL CYTOTOXICITY

(71) Applicant: Academia Sinica, Taipei (TW)

(72) Inventors: Han-Chung Wu, Taipei (TW); Ruei-Min Lu, New Taipei (TW); Chiung-Yi Chiu, Douliu (TW); I-Ju Liu, Taipei (TW); Yu-Ling Chang, New Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 15/563,950

(22) PCT Filed: Apr. 12, 2016

(86) PCT No.: PCT/US2016/027057
§ 371 (c)(1),
(2) Date: Oct. 3, 2017

(87) PCT Pub. No.: WO2016/168159
PCT Pub. Date: Oct. 20, 2016

(65) Prior Publication Data
US 2018/0127504 A1 May 10, 2018

Related U.S. Application Data

(60) Provisional application No. 62/147,344, filed on Apr. 14, 2015.

(51) Int. Cl.
*A61K 39/00* (2006.01)
*A61P 35/00* (2006.01)
*A61P 35/02* (2006.01)
*C07K 16/22* (2006.01)
*C07K 16/28* (2006.01)
*C07K 16/30* (2006.01)
*A61K 31/337* (2006.01)
*A61K 39/395* (2006.01)
*C12N 15/113* (2010.01)
*G01N 33/574* (2006.01)

(52) U.S. Cl.
CPC ........ *C07K 16/2863* (2013.01); *A61K 31/337* (2013.01); *A61K 39/3955* (2013.01); *A61P 35/00* (2018.01); *A61P 35/02* (2018.01); *C07K 16/22* (2013.01); *C07K 16/30* (2013.01); *C07K 16/3061* (2013.01); *C07K 16/3069* (2013.01); *C12N 15/1138* (2013.01); *G01N 33/57492* (2013.01); *A61K 2039/505* (2013.01); *C07K 2317/21* (2013.01); *C07K 2317/33* (2013.01); *C07K 2317/34* (2013.01); *C07K 2317/55* (2013.01); *C07K 2317/56* (2013.01); *C07K 2317/565* (2013.01); *C07K 2317/567* (2013.01); *C07K 2317/622* (2013.01); *C07K 2317/64* (2013.01); *C07K 2317/73* (2013.01); *C07K 2317/732* (2013.01); *C07K 2317/734* (2013.01); *C07K 2317/76* (2013.01); *C07K 2317/92* (2013.01); *C12N 2310/14* (2013.01); *C12N 2310/531* (2013.01); *G01N 2333/71* (2013.01)

(58) Field of Classification Search
CPC .... C07K 16/22; C07K 16/2863; C07K 16/30; C07K 2317/21; C07K 2317/33; C07K 2317/34; C07K 2317/55; C07K 2317/56; C07K 2317/565; C07K 2317/567; C07K 2317/622; C07K 2317/64; C07K 2317/73; C07K 2317/732; C07K 2317/76; C07K 2317/92; G01N 33/57492; G01N 2333/71; A61P 35/00; A61P 35/02; A61K 31/337; A61K 39/3955; A61K 2039/505
See application file for complete search history.

(56) References Cited

FOREIGN PATENT DOCUMENTS

| WO | 2002/020008 A1 | 9/2002 |
|----|----------------|--------|
| WO | 2014/055998 A1 | 4/2014 |

OTHER PUBLICATIONS

Paul, WE. Fundamental Immunology, 3rd ed. Raven Press, NY, Chap. 9, pp. 292-295, 1993.*
Rudikoff S. et al. Proc. Natl. Acad. Sci. USA, 79:1979-1983, 1982.*
Colman, PM. Research in Immunology, Elsevier, NY, 145(1):33-36, 1994.*
International Search Report for PCT/US2016/027057, dated Sep. 19, 2016.
Written Opinion of International Search Authority for PCT/US2016/027057, dated Sep. 19, 2016.
Franklin et al. "The Structural Basis for the Function of Two Anti-VEGF Receptor 2 Antibodies" Structure 19,1097-1107, Aug. 10, 2011.
Lu et al. "Selection of High Affinity Human Neutralizing Antibodies to 3 VEGFR2 From a Large Antibody Phage Display Library for Antiangiogenesis Therapy" (Int. J. Cancer: 97, 393-399 (2002)).

* cited by examiner

*Primary Examiner* — Robert S Landsman
(74) *Attorney, Agent, or Firm* — Hsiu-Ming Saunders; Intellectual Property Connections, Inc.

(57) ABSTRACT

An isolated antibody or an antigen-binding fragment thereof having a specific binding affinity to an epitope located within the domain 1 or domain 3 of human vascular endothelial growth factor receptor 2 (VEGFR2; SEQ ID NO: 74) is disclosed. The epitope within the domain 3 of the VEGFR2 is located between amino acid residues 250 and 270 of SEQ ID NO: 74. Use of the antibody or antigen-binding fragment thereof in the manufacture of a medicament for inhibiting tumor growth, tumor angiogenesis, and/or inducing cancer cell cytotoxicity in a subject in need thereof is also disclosed. Also disclosed is a method of detecting the presence of VEGFR2 in a tumor vascular endothelial cell or a cancer cell in a biological sample.

20 Claims, 9 Drawing Sheets

Specification includes a Sequence Listing.

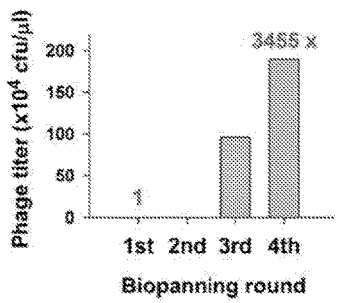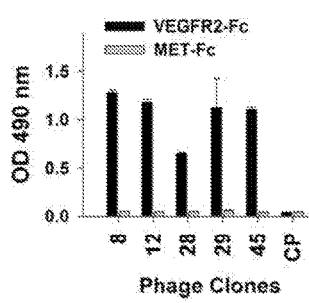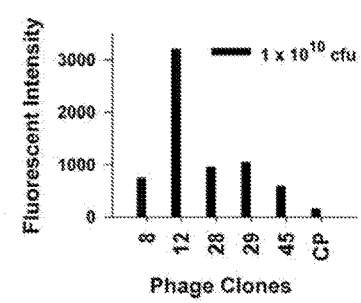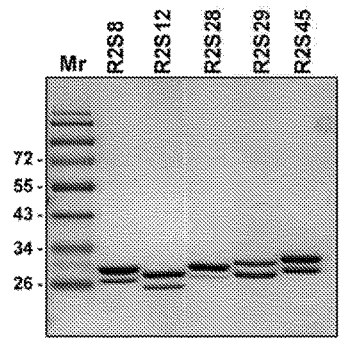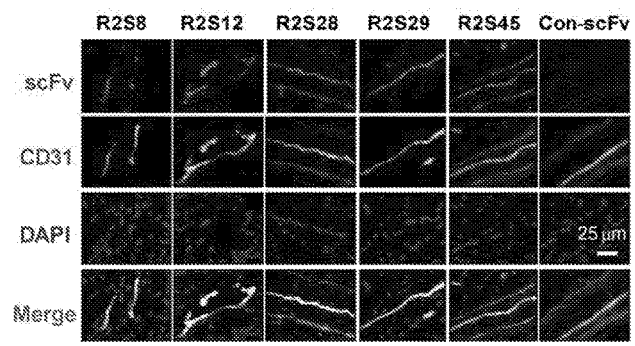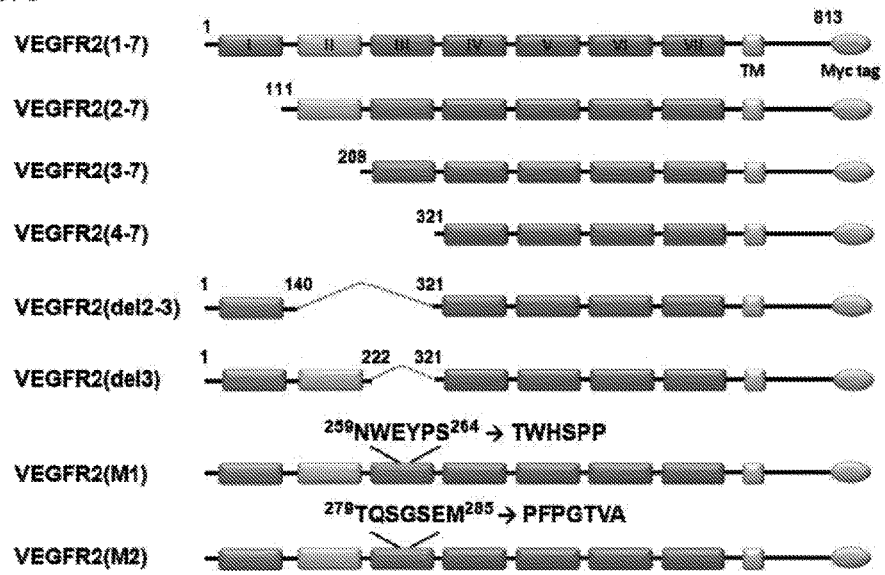

FIG. 3A
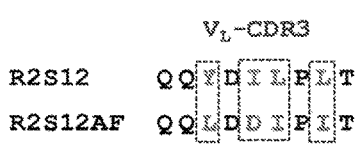
FIG. 3B
Kinetic constant of anti-VEGFR2 hAbs
| Antibody | $K_d$ (M) | $K_{on}$ (M$^{-1}$s$^{-1}$) | $K_{off}$ (s$^{-1}$) |
|---|---|---|---|
| Anti-VEGFR2 | $2.10 \times 10^{-9}$ | $2.25 \times 10^5$ | $4.72 \times 10^{-4}$ |
| Anti-VEGFR2-AF | $2.64 \times 10^{-10}$ | $1.67 \times 10^6$ | $4.42 \times 10^{-4}$ |
FIG. 3C
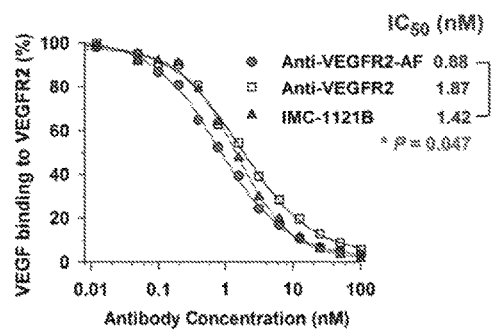
FIG. 3D
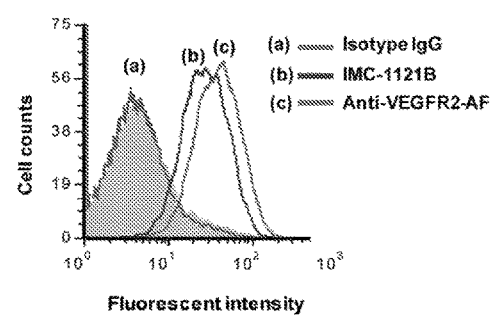
FIG. 9A
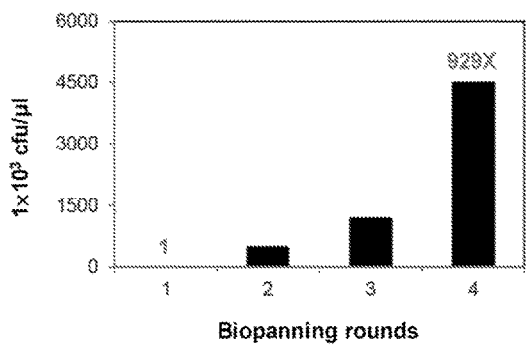
FIG. 9B
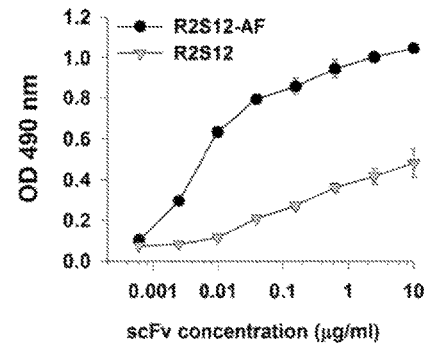

FIG. 11A
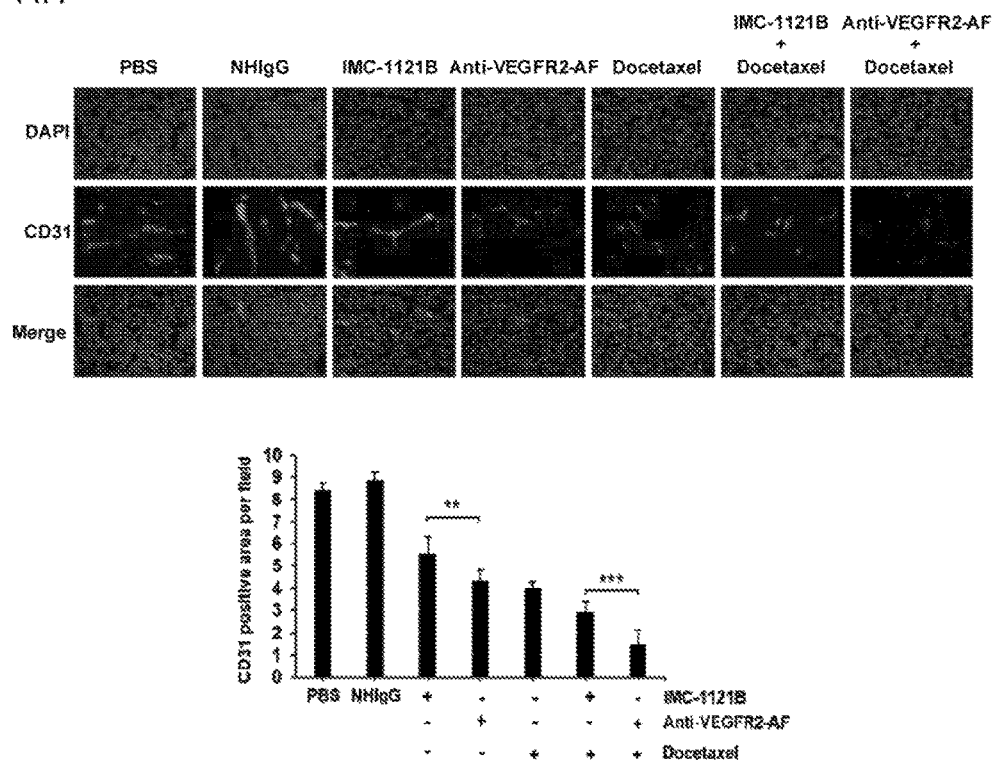
FIG. 11B
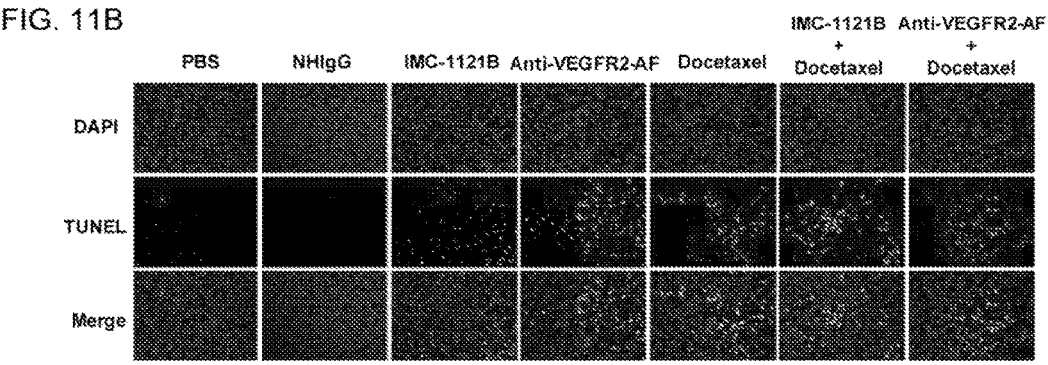
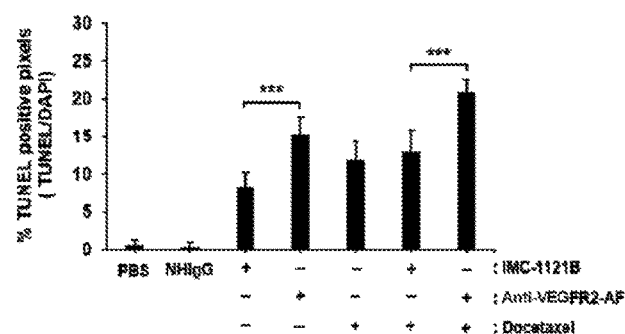

ANTI-VASCULAR ENDOTHELIAL GROWTH FACTOR RECEPTOR 2 (VEGFR2) ANTIBODY AND METHODS OF USE THEREOF FOR DETECTING VEGFR2 AND FOR INHIBITING TUMOR GROWTH, TUMOR ANGIOGENESIS AND/OR INDUCING CANCER CELL CYTOTOXICITY

REFERENCE TO RELATED APPLICATION

This application is a national stage application (under 35 U.S.C. 371) of PCT/US2016/027057 filed on 12 Apr. 2016, which claims priority to U.S. provisional application 62/147,344 filed on 14 Apr. 2015, all of which are herein incorporated by reference in their entireities.

FIELD OF THE INVENTION

The present invention relates generally to antibodies with anti-cancer activities, and more specifically to anti-VEGFR2 antibodies.

BACKGROUND OF THE INVENTION

Angiogenesis rarely occurs in adult healthy tissues. Vascular endothelial growth factor receptor 2 (VEGFR2) is expressed infrequently and at low levels in normal endothelial cells, as compared to tumor-associated endothelial cells. VEGFR2 expression is 3- to 5-folds higher in tumor vessels than that in normal vessels. Immunohistochemistry in biopsies of cancer patients further confirmed that VEGFR2 expression is significantly elevated in tumor vessels when compared with the vascular endothelium in normal tissues adjacent to the tumor region. Notably, expression of VEGFR2 is greater in high-metastatic tumor vessels than in low-metastatic tumor vessels.

VEGFR2 expression was originally shown to be restricted to the vessels of tumor tissues. However, recent studies have provided evidence that VEGFR2 is also present in malignant tumor cells. Circulating tumor epithelial cells in the blood of breast cancer patients were found to express VEGFR2, and thus such expression is associated with tumor metastasis and prognosis. Therefore, blocking VEGFR2-mediated signaling transduction to concomitantly inhibit tumor endothelial and malignant cells is considered an excellent strategy for the development of anticancer therapeutics.

The results from clinical studies indicate that fully human therapeutic antibodies against VEGFR2 are safe and well-tolerated. They show promise as an emerging therapy for cancer by blocking tumor angiogenesis. Therefore, development of a novel anti-VEGFR2 human antibody with enhanced therapeutic efficacy will benefit cancer patients.

SUMMARY OF THE INVENTION

In one aspect, the invention relates to an isolated antibody or an antigen-binding fragment thereof that has a specific binding affinity to an epitope located within the domain 1 or domain 3 of human vascular endothelial growth factor receptor 2 (VEGFR2; SEQ ID NO: 74), wherein the epitope within the domain 3 of the VEGFR2 is located between amino acid residues 250 and 270 of SEQ ID NO: 74.

In one embodiment of the invention, the epitope comprises the amino acid sequence of NWEYPS (SEQ ID NO: 66). The epitope does not comprise the amino acid sequence of GID, KH, or GLMTK (SEQ ID NO: 75).

In another embodiment of the invention, the antibody or antigen-binding fragment thereof of the invention exhibits a specific binding affinity to tumor vascular endothelial cells.

The antibody or antigen-binding fragment thereof of the invention comprises a heavy chain variable region ($V_H$) and a light chain variable region ($V_L$), the $V_H$ comprising $V_H$ CDR1, $V_H$ CDR2, and $V_H$ CDR3, and the $V_L$ comprising $V_L$ CDR1, $V_L$ CDR2, and $V_L$ CDR3, (i) wherein:
the $V_H$ CDR1, $V_H$ CDR2, and $V_H$ CDR3 comprise the amino acid sequence of SEQ ID NO: 1, SEQ ID NO: 2, and SEQ ID NO: 3, respectively; and the $V_L$ CDR1, $V_L$ CDR2, and $V_L$ CDR3 comprise the amino acid sequence of SEQ ID NO: 4, Ala Ala Ser, and SEQ ID NO: 5, respectively;

or (ii) wherein:
the $V_H$ CDR1, $V_H$ CDR2, $V_H$ CDR3 comprise the amino acid sequence of SEQ ID NO: 6, SEQ ID NO: 7, and SEQ ID NO: 8, respectively; and the $V_L$ CDR1, $V_L$ CDR2, and $V_L$ CDR3 comprise the amino acid sequence of SEQ ID NO: 9, Asp Ala Ser, and SEQ ID NO: 10 or 73, respectively;

or (iii) wherein:
the $V_H$ CDR1, $V_H$ CDR2, and $V_H$ CDR3 comprise the amino acid sequence of SEQ ID NO: 11, SEQ ID NO: 12, and SEQ ID NO: 13, respectively; and the $V_L$ CDR1, $V_L$ CDR2, and $V_L$ CDR3 comprise the amino acid sequence of SEQ ID NO: 14, Asp Ala Ser, and SEQ ID NO: 15, respectively;

or (iv) wherein:
the $V_H$ CDR1, $V_H$ CDR2, and $V_H$ CDR3 comprise the amino acid sequence of SEQ ID) NO: 16, SEQ ID NO: 17, and SEQ ID NO: 18, respectively; and the $V_L$ CDR1, $V_L$ CDR2, and $V_L$ CDR3 comprise the amino acid sequence of SEQ ID NO: 19, Gly Ala Ser, and SEQ ID NO: 20, respectively;

or (v) wherein:
the $V_H$ CDR1, $V_H$ CDR2, and $V_H$ CDR3 comprise the amino acid sequence of SEQ ID NO: 21, SEQ ID NO: 22, and SEQ ID NO: 23, respectively; and the $V_L$ CDR1, $V_L$ CDR2, and $V_L$ CDR3 comprise the amino acid sequence of SEQ ID NO: 24, Asp Ala Ser, and SEQ ID NO: 25, respectively.

In another embodiment of the invention, the $V_H$ CDR1, $V_H$ CDR2, and $V_H$ CDR3 comprise the amino acid sequence of SEQ ID NO: 6, SEQ ID NO: 7, and SEQ ID NO: 8, respectively; and the $V_L$ CDR1, $V_L$ CDR2, and $V_L$ CDR3 comprise the amino acid sequence of SEQ ID NO: 9, Asp Ala Ser, and SEQ ID NO: 10 or 73, respectively.

In another embodiment of the invention, the antibody or antigen-binding fragment thereof comprises: (a) a heavy chain variable region ($V_H$) comprising the amino acid sequence of SEQ ID NO: 76; and (b) a light chain variable region ($V_L$) comprising the amino acid sequence of SEQ ID NO: 77 or 78.

In another embodiment of the invention, the antibody or antigen-binding fragment thereof is a single-chain variable fragment, a Fab fragment, or a Fv fragment.

In another embodiment of the invention, the antibody or antigen-binding fragment thereof is a fully human antibody.

In another embodiment of the invention, the antibody or antigen-binding fragment thereof is labeled with a detectable compound or an enzyme.

In another aspect, the invention relates to a composition comprising a therapeutically effective amount of an antibody or antigen-binding fragment thereof of the invention and a pharmaceutically acceptable vehicle or carrier.

In one embodiment of the invention, the composition further comprises a chemotherapeutic agent. In one embodiment of the invention, the chemotherapeutic agent is docetaxel.

Further in another aspect, the invention relates to use of an antibody or antigen-binding fragment thereof or a composition of the invention in the manufacture of a medicament for inhibiting tumor growth, tumor angiogenesis, and/or inducing cancer cell cytotoxicity in a subject in need thereof.

In one embodiment of the invention, the tumor and/or cancer cell express VEGFR2. The use of the antibody or antigen-binding fragment thereof may further comprise use of an additional chemotherapeutic agent such as docetaxel in the manufacture of a medicament for inhibiting tumor growth, tumor angiogenesis, and/or inducing cancer cell cytotoxicity in the subject in need thereof.

Alternatively, the invention relates to an antibody or antigen-binding fragment thereof or a composition of the invention for use in inhibiting tumor growth, tumor angiogenesis, and/or inducing cancer cell cytotoxicity in a subject in need thereof.

The invention also relates to a method for inhibiting tumor growth, tumor angiogenesis, and/or inducing cancer cell cytotoxicity, comprising:
  administering to a subject in need thereof a composition comprising a therapeutically effective amount of an isolated antibody or antigen-binding fragment thereof of the invention and a pharmaceutically acceptable carrier, and thereby inhibiting tumor growth, tumor angiogenesis, and/or inducing cancer cell cytotoxicity in the subject in need thereof.

The method of the invention may further comprise administering to the subject in need thereof a composition comprising a therapeutically effective amount of a chemotherapeutic agent such as docetaxel. In one embodiment of the invention, the chemotherapeutic agent is simultaneously administered to the subject in need thereof.

In one embodiment of the invention, the tumor or cancer is at least one selected from the group consisting of pancreatic, breast, lung, leukemia, prostate and ovary cancer.

Yet in another aspect, the invention relates to a method of detecting the presence of VEGFR2 on tumor vascular endothelial cells or cancer cells in a biological sample, comprising:
  (i) admixing the antibody or antigen-binding fragment thereof of the invention with the biological sample,
  (ii) allowing the antibody or antigen-binding fragment thereof and the VEGFR2 on the tumor vascular endothelial cells or cancer cells in the biological sample to interact and form a complex; and
  (iii) detecting the presence of the VEGFR2 on the tumor vascular endothelial cells or cancer cells in the complex.

In one embodiment of the invention, the biological sample is a tissue specimen from a patient.

In another embodiment of the invention, the presence of the VEGFR2 on the tumor vascular endothelial cells or cancer cells in the complex is detected by immunoassay.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 1A-E show the results of selection and identification of phage-displayed scFvs against VEGFR2. (A) Phage display biopanning for VEGFR2-Fc recombinant protein. After four rounds of biopanning, the recovery rate of the phages was increased by 3,455-fold over that of the first round. cfu, colony-forming units. (B) Comparison of the binding of selected phage clones to VEGFR2-Fc protein by ELISA with a $1 \times 10^9$ cfu phage titer. (C) Cellular VEGFR2 binding affinity of phage clones were evaluated on HUVECs by flow cytometry with $1 \times 10^{10}$ cfu.(D) Soluble anti-VEGFR2 scFvs were purified and analyzed by SDS-PAGE with Coormassie blue staining. (E) Immunofluorescent staining for human tumor vasculature, Frozen sections of surgical specimens of lung cancer patients were probed with anti-V.EGFR2 scFvs, followed by anti-E, tag antibody and rhodamine-conjugated secondary antibody staining. Vascular endothelium was stained with anti-human CD31 antibody, and then incubated with FITC-conjugated secondary antibody. Nuclei were stained with DAPI; Con-scFv, control scFv.

FIGS. 3A-D show affinity maturation of anti-VEGFR2 hAb, and analysis of anti-VEGFR2-AF hAb activity. (A) Amino acids of the light chain variable domain of CDR3 ($V_L$-CDR3) of R2S12 (SEQ ID NO: 10) and R2S12AF (SEQ ID NO: 73). Residues that differ between R2S12 and R2S12AF are boxed. (B) Kinetic constants of anti-VEGFR2 and anti-VEGFR2-AF hAb, as determined using purified IgG and a BIACORE T100™. The $K_d$ value was calculated using BIACORE T100™ evaluation software. (C) Competitive ELISA was performed to examine dose-dependent inhibition of VEGF-A binding to VEGFR2 by human antibody. A value of 100% was attributed to the binding of 4 nM VEGF-A to immobilized VEGFR2 in the absence of competitors. Error bar, SD; n=4. (D) Determination of the binding activity of anti-VEGFR2 antibody to HUVEC by flow cytometry analysis. Antibody concentration: 0.1 μg/ml.

FIG. 8 shows construction of VEGFR2-expressing vectors. Schematic presentation of constructs expressing deletion or substitution mutants of human VEGFR2 domains. There are seven immunoglobulin-like domains in the extracellular region of VEGFR2, which are labeled I to VII. TM: transmembrane domain. The sequence identifiers of $^{259}$NWEYPS$^{264}$, $^{261}$TWHSPP$^{266}$, $^{279}$TQSGSEM$^{285}$, and $^{281}$PFPGTVA$^{287}$ are SEQ ID NO: 66, SEQ ID NO: 68, SEQ ID NO: 67, and SEQ ID NO: 69, respectively.

FIGS. 9A-B show the results of selection and identification of scFvs against VEGFR2 using a phage-displayed synthetic scFv library. (A) Affinity maturation for R2S12. The phage-displayed R2S12-$V_L$-CDR3 mutagenic scFv library was incubated for 1 hour at 4° C. with 0.1 μg VEGFR2-Fc immobilized on Protein G DYNABEADS®. Subsequently, the beads were washed four times with PBS containing 1% TWEEN™ 20. After four rounds of biopanning, the recovery rate of the phages was increased by 929-fold over that of the first round. (B) Comparison of the binding activity of the indicated concentrations of R2S12 and R2S12-AF scFv to VEGFR2-Fc protein, as assayed by ELISA. Error bar, SE.

FIGS. 11A-B show investigation of vascular endothelium and apoptotic cells in tumor tissue after drug treatment. Frozen tumor sections were prepared from mice of each group at the end of the treatment period. (A) Sections were stained with anti-CD31 antibody to visualize tumor blood vessels. CD31-positive endothelium was quantitatively measured using ImageJ software. (B) Apoptotic cells in frozen tumor sections were analyzed using TUNEL assay. The apoptotic cells were quantified using ImageJ software. The sections were stained with DAPI for indication of all cells. n=5; Scale bar, 100 μm; 200× magnification; Error bar, SE; , P<0.01; *, P<0.001.

DETAILED DESCRIPTION OF THE INVENTION

Figure 2A:
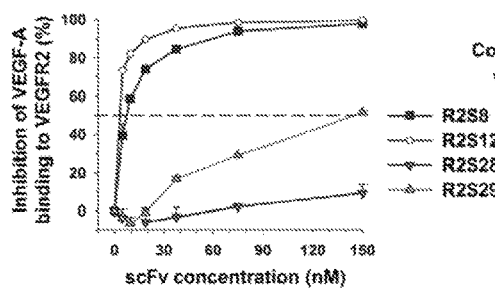
FIGS. 2A-F show that anti-VEGFR2 scFv suppresses VEGF-A binding and activation of VEGFR2 in HUVECs. (A) Analysis of the competition ability of anti-VEGFR2 scFv with VEGF-A by ELISA. The amount of VEGF-A binding to immobilized VEGFR2 in the absence of competitors was considered to be 100%. (B) Phosphorylated VEGFR2 (Pho. VEGFR2) expression in HUVECs treated with VEGF-A and scFv competitors was detected by Westernblot. Quantification of phosphorylated VEGFR2 was based on luminescence intensity, and normalized to total VEGFR2. (C to F) Epitope mapping of R2S12. (C) Sequence alignment of VEGFR2 domain 3 (VEGFR2-D3) of human (from 221 a.a. to 320 a.a. of SEQ ID NO: 74) and mouse (from 223 a.a. to 322 a.a. of SEQ ID NO: 80). Residues that differ between the two species are boxed. The residues involved in mutants M1 and M2 are underlined. The filled and open circles are used to indicate human VEGFR2-D3 residues in contact with 1121B and 6.64 antibodies, respectively. (D) Graphic depicting the VEGFR2-D3 backbone; NWEYPS (SEQ ID NO: 66) residues (M1) responsible for R2S12 binding are highlighted. (E) Model of the surface of VEGFR2-D3. NWEYPS (SEQ ID NO: 66) residues, i.e., the M1 area, is delineated by the black line. (F) The residues that make contact with 1121B and 6.64 on the surface of VEGFR2-D3 are indicated. The contacting residues of 1121B, which are localized in the M1 area, are also indicated. (N, N terminus; C, C terminus.)

Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Additionally, some terms used in this specification are more specifically defined below.

Definitions

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

The term "treating" or "treatment" refers to administration of an effective amount of the compound to a subject in need thereof, who has cancer, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

"An effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The term "chemotherapeutic agent" refers to a pharmacological agent that is known to be of use in the treatment of cancer.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

HED=animal dose in mg/kg×(animal weight in kg/human weight in kg)$^{0.33}$.

Ramucirumab (i.e., IMC-1121B) trade name is CYRAMZA®.

Human vascular endothelial growth factor receptor 2 (VEGFR2) domain 1 region is from 45 a.a. to 110 a.a., and domain 3 is from 224 a.a. to 320 a.a.

Sequence Identifiers:
QQLDDIPIT (R2S12AF variable light chain CDR3; SEQ ID NO: 73); VGFR2 (HUMAN Vascular endothelial growth factor receptor 2; SEQ ID NO: 74); GLMTKK (SEQ ID NO: 75);

The $V_H$ region of R2S12 and R2S12-AF are the same (SEQ ID NO: 76): QVNLRESGGGLVKPGGSLRLS-CAASGFTFGSYTMNWVRQAPGKGLEWVA-SITSGSSYIFYTDSVKGRFIISRDNSRSSLFLQMNSL-RAEDTAIYYCARGSASAFDIWGQGTMVTVSS;

The $V_L$ region of R2S12 (SEQ ID NO: 77): DIQMTQSPSSLSASVGDRVTITCKASDDIINYLNWY-QQKPGEAPKLLIYDASILETGVPSRFSGSGSGTDFT-FTISSLQPEDIATYYCQQ<u>YDILPL</u>TFGGGTKLEIK;

The $V_L$ region of R2S12AF (SEQ ID NO: 78): DIQMTQSPSSLSASVGDRVTITCKASDDIINYLNWY-QQKPGEAPKLLIYDASILETGVPSRFSGSGSGTDFT-FTISSLQPEDIATYYCQQ<u>LDDIP</u>ITFGGGTKLEIK; The amino acid residues that are different between R2S12 $V_L$ and R2S12AF $V_L$ are underlined above.

Human IgG1 constant region (SEQ ID NO: 79); Mouse VEGFR2 amino acid sequence (SEQ ID NO: 80).

Abbreviation: complementarity determining regions (CDRs); Fab (fragment, antigen-binding region); $F_V$ region (variable domain).

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods
Isolation of Phages Binding to VEGFR2 from a Phage-displayed scFv Library A human naïve phage-displayed scFv library with 6×10$^{10}$ complexity previously established in our laboratory was used for selection. The scFv library was subtracted non-specific binding with protein G DYNABEADS® (Invitrogen), and subsequently incubated with VEGFR2-Fc recombinant protein (R&D Systems)-immobilized DYNABEADS®. After washing with PBS containing 0.1% TWEEN™ 20 (PBST0.1), phages bound to VEGFR2-Fc were recovered by infection with *E. coli* TG1 cells. After determination of phage titer, the next round of biopanning was performed.

Competitive VEGF Binding Assay

Various concentrations of anti-VEGFR2 scFvs were mixed with 3 nM human VEGF-A (Peprotech), and added to 96-well plates coated with 1 µg/ml of VEGFR2-Fc and pre-blocked in 1% BSA. After incubation for 1 hr at RT and washes with PBST, the bound VEGF molecules were detected using anti-VEGF mAb (GeneTex) and HRP-labeled goat anti-mouse IgG. The reaction was developed with a mixture of OPD and $H_2O_2$, and subsequently terminated with 3 N HCl. The absorbance was determined using a microplate reader at 490 nm.

Human Tumor Vasculature Staining with Anti-VEGFR2 scFvs

Human lung cancer surgical specimens were obtained from the Department of Pathology, National Taiwan University Hospital. Frozen section slides were washed with PBS and then fixed with paraformaldehyde. After washing with PBS, slides were blocked with normal horse serum (Vector), and incubated with the scFv. After washing with PBST, a mixture of rabbit anti-E tag antibody (Bethyl Laboratories) and mouse anti-human CD31 mAb (BD) was added, and the slides were incubated for 1 hr. The coverslips were stained for 1 hour with FITC-labeled anti-mouse IgG, rhodamine-labeled goat anti-rabbit IgG, and DAPI, and captured using an Inverted Fluorescence Microscope (Zeiss, Axiovert 200M).

Tube Formation Assay

MATRIGEL® (BD Biosciences) was thawed at 4° C. overnight, and 10 μl MATRIGEL® was added to each well of a pre-chilled μ-Slide Angiogenesis (Ibidi); the slide was then incubated at 37° C. for 15 minutes. Starved HUVECs ($4 \times 10^4$ cells) were added to EBM-2 containing 0.2% serum with or without 40 ng/ml VEGF-A and anti-VEGFR2 antibodies. After 24 hours of incubation, endothelial cell tube formation was assessed with an OLYMPUS inverted microscope and digital camera (OLYMPUS, DP-12). Tubular lengths and branching points were quantitatively evaluated with ImageJ software. Inhibition percentage by antibodies was expressed as a percentage of that in VEGF-A-treated wells without competitor.

Clinical Data Set Analysis

Raw microarray data were downloaded from the Gene Expression Omnibus at the National Center for Biotechnology Information (NCBI) website. Raw data were normalized. GEO profile GDS2545/1954_at/KDR was used for metastatic prostate cancer analysis.

Construction and Expression of Anti-VEGFR2 Human Antibody

The $V_H$ region of R2S12, R2S12-AF, and IMC-1121B (Lu et al., (2003) "Tailoring in vitro selection for a picomolar affinity human antibody directed against vascular endothelial growth factor receptor 2 for enhanced neutralizing activity" J Biol Chem 278, 43496-43507) were cloned separately into modified expression vector pcDNA5-FRT-Gammal with a signal peptide and human IgG1 constant region, using AgeI and NheI sites. In addition, the $V_L$ region of R2S12, R2S12-AF, and IMC-1121B were separately cloned into modified expression vector p-Kappa-HuGs, using AgeI and EcoRV sites. Both heavy and light chain gene-containing plasmids were combined into a biscistronic vector to generate a single vector system. The plasmids were transfected into FLPIN™-CHO cells (Invitrogen). The transfected cells were selected using hygromycin B after 2-3 weeks to establish stable clones; these clones were cultured in SFM4CHO media (Thermo Scientific) to produce human antibodies. After 2 weeks of incubation, cultured media of stable clones was collected, centrifuged, and filtered through a 0.45 μm membrane. The supernatant was then subjected to protein G column chromatography (GE healthcare) for purification of anti-VEGFR2 human IgG. After dialysis of eluents with PBS, the concentration of antibody was assessed using Bradford reagent (Thermo Scientific) and spectrophotometry.

Affinity Maturation of Anti-VEGFR2 Human IgG

Affinity maturation was performed as previously described. Briefly, we constructed a synthetic phage-displayed scFv library comprised of the $V_H$ and $V_L$ gene repertoire of R2S12, with random mutations introduced at seven amino acid residues of $V_L$-CDR3. This synthetic library was used to perform biopanning for VEGFR2-Fc-immobilized DYNABEADS®. After four to five rounds of stringent in vitro biopanning, positive clones were screened and identified by ELISA. Superior VEGFR2-binding clones were identified through comparison to the respective parental clone.

Measurement of Binding Kinetics

The affinity and kinetics of anti-VEGFR2 antibodies were measured by surface plasmon resonance in a BIACORE T100™ (GE healthcare). VEGFR2-Fc protein was coupled to an EDC- and NHS-activated CM5 sensor chip in a BIACORE flow cell, and then blocked with ethanolamine according to the manufacturer's directions. Associated and dissociated phases were monitored under continuous flow of 30 μl/min, using antibody concentrations ranging from 0.1 to 100 nM for 5 min. Regeneration was performed by injection of regenerate buffer (0.2 M NaCl, 10 mM glycine, pH 2.7). To determine binding constants, the sensorgrams were fit globally to a sample 1:1 interaction model using BIAevaluation software (GE healthcare).

Animal Models

Procedures involving animals and their care were conducted according to the guidelines of the Academia Sinica Institutional Animal Care and Utilization Committee in compliance with national and international laws and policies. Non-obese diabetic-severe combined immunodeficiency (NOD/SCID) mice were purchased from the National Laboratory Animal Center (Taiwan). The human prostate cancer xenograft tumor model was developed by subcutaneously injecting $2 \times 10^6$ PC-3 cells into the dorsal flank of a six-week old male mouse. Animals were monitored daily for general health, and body weights were measured twice weekly. Tumor size was measured with slide calipers and calculated as length×width$^2$×0.52. Mice with size-matched tumors (50 mm$^3$) were randomly assigned to different treatment groups (n=9) and intravenously injected with normal human IgG (NHIgG; Jackson ImmunoResearch), IMC-1121B, anti-VEGFR2-AF antibodies, or an equivalent volume of PBS through the tail vein. An antibody dose of 20 mg/kg was injected twice a week for four weeks. For combination therapy, docetaxel (ScinoPharm Taiwan) was also intravenously administered at a dose of 5 mg/kg once a week for three weeks. At the end of the experiment, tumor tissue and visceral organs were removed and fixed for histological analysis.

For systemic leukemia engraftment studies, NOD/SCID/ IL2Rγ-/- (NSG) mice were obtained from the Animal Center of the Institute of Cellular and Organismic Biology, Academia Sinica. Six-week old females were intravenously injected with $5 \times 10^6$ HL-60 cells through the tail vein. Animals were monitored daily for general health, and body weights were measured twice weekly. At 3 days after tumor inoculation, mice were randomly selected (n=9) for intravenous injection with 20 mg/kg NHIgG, IMC-1121B, anti-VEGFR2-AF antibodies, or an equivalent volume of PBS, twice weekly. Mice were observed daily for signs of toxicity, and the survival times were recorded. At the end-point of treatment, the visceral organs of each mouse were removed and fixed for further histological examination.

Cell Culture

HUVEC (human umbilical vascular endothelial cells) were purchased from LONZA. HL-60 (human promyelocytic leukemia), PC-3 (human prostate cancer), EA.hy926 (human umbilical vein cell line), and 293T (human embryonic kidney cell) cell lines were obtained from the American Type Culture Collection (ATCC®). The hESC-H9 (human embryonic stem cell) line was purchased from WiCell, and the FLP-IN™-CHO cell line was obtained from Invitrogen. HUVECs were cultured in endothelial growth medium (EBM-2, LONZA). HL-60 and PC-3 cells were cultured in RPMI 1640 medium (GIBCO™). EA.hy926 and 293T cells were cultured in DMEM (GIBCO™). FLP-IN™-CHO cells were maintained in Ham's F12 medium. The hESC-H9 line was cultured as previously described. All cell lines were maintained in conditioned media supplemented with 10% fetal bovine serum (FBS; GIBCO™) and 100 µg/ml Penicillin/Streptomycin (P/S; GIBCO™) in a humidified incubator with 5% $CO_2$ at 37° C.

Screening of Anti-VEGFR2 Phage Clones by ELISA

The selected phages were further examined by ELISA screening. The 96-well plates were coated with 1 µg/ml of VEGFR2-Fc, Met-Fc (R&D), or BSA (Sigma) protein in 0.1 M sodium bicarbonate overnight at 4° C. After blocking with 1% BSA in PBS (w/v) for 2 hr at room temperature, 70-randomly selected phage clones were added to the plates at a 1:2 dilution in 1% BSA, and incubated for 1 hr at room temperature. Following washes with PBST, the plates were incubated with a 1:2000 dilution of horseradish peroxidase (HRP)-conjugated mouse anti-M13 phage antibody (GE) for 1 hr. After washing with PBST, the colorimetric reaction was developed with the peroxidase substrate ortho-phenylenediamine (OPD; Sigma) plus $H_2O_2$ for 15 min, and then terminated by the addition of 3 N HCl. The absorbance at 490 nm was determined using a microplate reader (SpectraMax, Molecular Devices). Plasmid DNA of positive clones were isolated and sequenced using the pCANTAB5 sequencing primer set.

Plasmid Construction

Human cDNA clone encoding the full-length VEGFR2 sequence (NM_002253.2) was purchased from Thermo Seientifics, and used as a PCR template for the following constructs. Various lengths of the VEGFR2 extracellular region with signal peptide, transmembrane domain, and truncated cytoplasmic domain were constructed, as follows (see also FIG. 8): VEGER2(1-7), full-length extracellular region of VEGFR2, comprised of domains 1-7 from residues $Met^1$ to $Leu^{813}$; VEGFR2(2-7), containing domains 2-7 from residues $Ala^{111}$ to $Leu^{813}$; VEGFR2(3-7), containing domains 3-7 from residues $Ser^{208}$ to $Leu^{813}$; VEGFR2(4-7), containing domains 4-7 from residues $Phe^{321}$ to $Leu^{813}$; VEGFR2(del2-3), in which domains 2 and 3 of VEGFR2 were deleted by ligation of two fragments encoding domain 1 ($Met^1$ to $Glu^{140}$) and domains 4-7 ($Phe^{321}$ to $Leu^{813}$); VEGFR2(del3), in which domain 3 of VEGFR2 was deleted by ligation of two fragments encoding domains 1-2 ($Met^1$ to $Arg^{222}$) and 4-7 ($Phe^{321}$ to $Leu^{813}$); VEGFR2(M1), a mutagenic construct containing all seven domains of the full-length extracellular region a VEGFR2 ($Met^1$ to $Leu^{813}$), in which $^{259}NWEYPS^{264}$ (SEQ ID NO:66) in domain 3 is replaced with $^{261}TWYHSPP^{266}$ (SEQ ID NO; 68) of the mouse homolog; and VEGFR2 (M2), amutagenic construct containing all seven domains of the full-length extracellular region of VEGFR2 ($Met^1$ to $Leu^{813}$), in which $^{279}TQSGSEM^{285}$ (SEQ ID NO: 67) in domain 3 is replaced by $^{281}PFPGTVA^{287}$ (SEQ ID NO: 69) of the mouse homolog.

Expression and Purification of Soluble scFv

E. coli strain HB2151 was infected with anti-VEGFR2 scFv phage clone PC-8, 12, 28, 29, or 45, and periplasmic extracts of bacteria were prepared. Soluble scFv was purified in periplasmic extracts using protein L agarose columns (Thermo Scientific) according to the manufacturer's instructions. Purified scFvs were completely dialyzed with PBS, and analyzed by reducing SDS-PAGE followed by Coomassie blue staining.

Proliferation Assay

A total of $1\times10^4$ HUVECs were seeded onto 96-well plates overnight. The cells were then starved in serum-free EBM-2 overnight. Subsequently, 8 µg/ml of the selected scFv, together with 40 ng/ml VEGF in low-serum EBM-2 (0.2%), was added to the wells, and then incubated for 48 hours. Cell proliferation was assessed using MTT reagent (Invitrogen), according to the manufacturer's instructions.

Flow Cytometry Analysis

About $1\times10^4$ HUVEC were incubated with the selected anti-VEGFR2 phage clones at 4° C. for 1 hour in FACS buffer (PBS containing 1% fetal bovine serum). After the cells were washed with FACS buffer, they were first incubated with mouse anti-M13 phage Ab for 1 hr at 4° C., and then with R-phycoerythrin-conjugated goat anti-mouse IgG (Jackson Immuno Research) for 30 min at 4° C. Flow cytometry was performed with a FACSCantoII (BD), and emission fluorescence intensity was measured with FACS Diva software (BD) to quantitatively compare binding affinities.

Lentivirus-mediated Short Hairpin RNA (shRNA) Knockdown

The lentiviral vector pLKO_TRCN0000199129, which encodes shRNA sequence, ccggcgctgacatgtacggtc tat gctcgagca tag accgta cat gtcagcgttttttg (SEQ ID NO: 70), and targets human VEGFR2, was obtained from the National RNAi Core Facility (Academia Sinica, Taiwan). The pLKO_TRCN0000072249 vector encoding shRNA against firefly luciferase was used as a negative control. For virus production, pLKO vector, the envelope plasmid pMD.G, and the packing plasmid pCMV-ΔR8.91 were co-transfected at a ratio of 10:1:9 into 293T cells using LIPOFECTAMINE® 2000 (Invitrogen). At 18 hours post-transfection, culture media were re-placed with fresh DMEM plus 10% FBS and 1% BSA. The supernatant containing virus particles was harvested after incubation for 24 and 48 hours.

PC-3 cells were seeded at a density of $1\times10^6$ cells in a 60-mm dish one day before lentivirus transduction. Virus-containing media supplemented with 8 µg/ml polybrene (Sigma-Aldrich) was added to PC-3cells, and incubated for 24 hours. Subsequently, the transduced cells were selected by incubation in growth media containing 2 µg/ml puromycin for 3 days.

Imnunohistochemical Staining

Iminunohistochemical staining was carried out as previously described. Briefly, sections were deparaffinized and rehydrated, and antigen retrieval was performed concomitantly using Trilogy buffer (Cell Marque). Endogenous peroxidase activity was then blocked by incubation in 3% $H_2O_2$ in methanol for 30 minutes. After washes with PBS, sections were incubated with 1% BSA for 30 min to block nonspecific binding. Sections were then incubated with anti-VEGFR2 antibody (55B11, Cell Signaling) for 1 hr at room temperature. After washing with PBST0.1, sections were treated with the polymer-based Super Sensitive detection system (Biogenex, San Ramon) according to the manufacturer's instructions. Horseradish peroxidase activity was detected by the development of color with chromogenic substrate diaminobenzidine hydrochloride (DAB) (0.02%). The slides were lightly counterstained with hematoxylin (Sigma-Aldrich), mounted with Permount (Fisher Scientific), and examined by light microscopy.

Western Blot Analysis

Western blots were performed using standard protocols, as previously described. The primary antibodies were purchased from Cell Signaling Technology and used at a 1,000-fold dilution for protein detection; the antibodies used are as follows: anti-VEGFR2 (clone 55B11), anti-phospho-VEGFR2 (Tyr1175; clone 19A10), anti-FAK, anti-phospho-FAK (Tyr397; cloneD20B1), anti-p42/44 MAPK, anti-phospho-p42/44 MAPK (Thr202/Tyr204; cloneD13.14.4E), anti-Akt, and anti-phospho-Akt (Ser473).

Immunofluorescence Assay of Frozen Tissue Sections

For tumor blood vessel studies, samples were fixed in OCT. Frozen blocks were cut into 50 μm sections, and frozen tumor tissue sections were fixed with 1% paraformaldehyde, permeabilized with 0.1% TRITON™-X 100, blocked with normal horse serum (Vector), and then incubated for 1 hour at room temperature (RT) with a 1:100 dilution of the primary antibody (rat anti-mouse CD31 (PECAM-1); BD Bioscience). Subsequently, the tissue sections were incubated with Alexa 549-conjugated goat anti-rat antibody (Invitrogen) at room temperature for 1 hour. Nuclei were stained with DAPI, and sections were then mounted with fluorescent mounting solution. Immunofluorescent images were acquired using a Zeiss Axiovert 200M microscope. Positive areas of CD31 endothelial cells were quantified by pixel area counting and normalized with DAPI staining using ImageJ software under low power magnification.

Terminal Deoxynucleotidyltransferase-mediateddUTP Nick End Labeling (TUNEL)

The frozen tumor tissue sections were fixed with 1% paraformaldehyde and permeabilized with 0.1% TRITON™-X 100, before being incubated with terminal deoxynucleotidyltransferase-mediated dUTP nick end labeling reaction mixture (Roche Diagnostics) at 37° C. for 1 hour. After washing three times with PBS, the slides were incubated with FITC-anti-DIG antibody (1:2000) and DAPI (1:500). Slides were mounted with mounting solution and visualized under a fluorescent microscope. Slides were independently examined by three individuals. Areas with TUNEL-positive cells were quantified by pixel area counting, and normalized to DAPI staining using ImageJ software.

Hematoxylin and Eosin (H&E) Staining

Tumors and indicated organs were dissected from mice and fixed in 4% paraformaldehyde overnight. Fixation and processing of specimens were performed in accordance with standard procedures. The specimens were embedded in paraffin and cut into 50 μm sections. Rehydrated paraffin-embedded tissue sections were stained with Mayer's hematoxylin solution (Wako) for 5 minutes and washed with water for 1-2 minutes. The slides were then stained with eosin solution (Wako) for 10 minutes. Tissues were visualized with Tissue Gnostics microscopes.

Quantitative RT-PCR

Total RNA extractions were performed using TrizolRNA isolation reagent (Invitrogen). Subsequently, cDNA was synthesized using oligo(dT) primers (Fermentas) and Super Script III reverse transcriptase (Invitrogen), according to the manufacturer's instructions. The forward and reverse primers used to amplify VEGFR2 cDNA through PCR are as follows: VEGFR2-F: gaacatttgggaaatctcttgc (SEQE ID NO: 71); VEGFR2-R: cggaagaacaatgtagtctttgc (SEQ ID NO: 72). Quantitative PCR was performed using the LightCycler480 System (Roche Applied Science). The transcript levels of VEGFR2 were normalized to those of GAPDH in the same sample. The ratio values were calculated accordingly for each sample. The reactions were performed in triplicate.

Results

Identification of Phage-displayed scFv that Binds to VEGFR2

A phage-displayed human naïve scFv library was used to isolate phages that bind to VEGFR2 recombinant protein. After four rounds of affinity selection (biopanning), the titer of bound phage increased by as much as 3,455-fold (FIG. 1A). Through ELISA screening and DNA sequencing, we identified five distinct phage clones (R2PC8, R2PC12, R2PC28, R2PC29, R2PC45; Table 1) that bind highly to VEGFR2-Fc, but not to c-Met-Fe control protein (FIG. 1B). We then used FACS assay of human umbilical vein endothelial cells (HUVEC) to confirm that all five clones have the ability to bind to VEGFR2 on the cell surface; of the five clones, R2PC12 exhibited the greatest reactivity (FIG. 1C). Table 1 shows the amino acid sequence of $V_H$ and $V_L$ domains of anti-VEGFR2 scFvs.

TABLE 1

| | FR1 (SEQ ID NO: ) | CDR1 (SEQ ID NO: ) | FR2 (SEQ ID NO: ) | CDR2 (SEQ ID NO: ) |
|---|---|---|---|---|
| | $V_H$ domains | | | |
| R2PC8 | QVQLVQSGGGLVKPGGSLRLSCAAS (26) | GFITSSYS (1) | MSWAIRQAPGKGLEWVSS (27) | ISSSSSYI (2) |
| R2PC12 | QVNLRESGGGLVKPGGSLRLSCAAS (34) | GFTFGSYT (6) | MNWVRQAPOKGLEWVAS (35) | ITSGSSYI (7) |
| R2PC28 | EVQLVESGGALVQPGGSLRLSCVGS (42) | EFTFSHYN (11) | LHWVRQAPGKGLEWLAV (43) | ISDDGRNK (12) |
| R2PC29 | QVQLQQSGAEMKKSGSSVKVSCKAS (50) | GGNFISKG (16) | ISWVRQAPGQGLEWMGG (51) | IIPLFGTG (17) |
| R2PC45 | QVNLRESGGGVVQPGRSLRLSCAAS (58) | GFTFSSYA (21) | MHWVRQAPGKGLEWVAV (59) | ISYDGSNK (22) |

| | FR3 | CDR3 | FR4 | Family |
|---|---|---|---|---|
| R2PC8 | YYADSVKGRFTISRDNAKNSLYLQMNSLRAEDTAVYYC (28) | ARSTDAFDI (3) | WGQGTMVTVSS (29) | $V_H3$ |
| R2PC12 | FYTDSVKGRFTISRDNSRSSLFLQMNSLRAEDTAIYYC (36) | ARGSASAFDI (8) | WGQGTMVTVS S (37) | $V_H3$ |

TABLE 1-continued

| | FR1 | CDR1 | FR2 | Family |
|---|---|---|---|---|
| R2PC28 | YYGDSVKGRFTISRDNSKN TLYLQMNGLRAEDTAVYY C (44) | ARVPTVWRG GVYDI (13) | WGQGTMVTVS S (45) | $V_H 3$ |
| R2PC29 | NYAQKFQGRVTITADESTT TVYLQLTSLTPEDTAMYFC (52) | ATADVDYSDS LEAFDM (18) | WGQGTMVTVS S (53) | $V_H 1$ |
| R2PC45 | YYADSVKGRFTISRDNSKN TLYLQMNSLRAEDTAVYY C (60) | AREQDYGSSS GDAFDI (23) | WGQGTMVTVS S (61) | $V_H 3$ |

$V_L$ domains

| | FR1 | CDR1 | FR2 | CDR2 |
|---|---|---|---|---|
| R2PC8 | DIVMTQSPSSLSASVGDRVTI TCRAS (30) | QRISNY (4) | LNWYQHKSGE DPKLLIY (31) | AAS (Ala Ala Ser) |
| R2PC12 | DIQMTQSPSSLSASVGDRVTI TCKAS (38) | DDIINY (9) | LNWYQQKPGE APKLLIY (39) | DAS (Asp Ala Ser) |
| R2PC28 | EIVLTQSPATLSLSPGERATL SCRAS (46) | QSVGSY (14) | LAWYQQRPGQP PRLLIY (47) | DAS (Asp Ala Ser) |
| R2PC29 | DIVMTQSPSSLSASVGDRVTI TCRAS (54) | QSINNY (19) | LNWYQQKPGK APNLLIY (55) | GAS (Gly Ala Ser) |
| R2PC45 | DIQMTQSPSSLSASVGDRVTI TCRAS (62) | QRISSY (24) | LNWYQQKPGK APKLLIY (63) | DAS (Asp Ala Ser) |

| | FR3 | CDR3 | FR4 | Family |
|---|---|---|---|---|
| R2PC8 | SLQSGVPSRFSGSGSGTDFTL TISSLQPEDFATYYC (32) | QQYDRYPPT (5) | FGQGTKLEIK (33) | $V_\kappa 1$ |
| R2PC12 | ILETGVPSRFSGSGSGTDFTF TISSLQPEDIATYYC (40) | QQYDILPLT (10) | FGGGTKLEIK (41) | $V_\kappa 1$ |
| R2PC28 | NRATGVAARFSGSGSGTDFT LTIDSLEAEDAATYYC (48) | HQSSSLPRT (15) | FGQGTKLEIK (49) | $V_\kappa 3$ |
| R2PC29 | SLQSGVPSRFRGSGSGTDFTL TISSLQPEDFATYYC (56) | QQSYSTPL (20) | FGQGTKLEIK (57) | $V_\kappa 1$ |
| R2PC45 | NLQSGVPSRFSGSGSGTDFTL TINGLQPDDFAIYFC (64) | HQSYSAPPT (25) | FGQGTKVEIK (65) | $V_\kappa 1$ |

Complementarity-determining regions 1-3 (CDR1-3) and framework regions 1-4 (FR1-4) for both the $V_H$ and $V_L$ domains are shown. The V domain families were aligned by IMGT database Subsequently, we generated soluble scFv proteins from the five VEGFR2-binding phage clones, which were designated as R2S8, R2S12, R2S28, R2S29, and R2S45 (FIG. 1D). The binding ability of the anti-VEGFR2 scFvs to tumor vascular endothelium in human lung cancer surgical specimens was investigated through the use of immunofluorescence staining assays. We observed that the fluorescent signals of anti-VEGFR2 scFvs apparently colocalize with endothelial cell marker CD31 (FIG. 1E), suggesting that these scFvs are able to specifically recognize tumor vasculature.

Figure 2B:
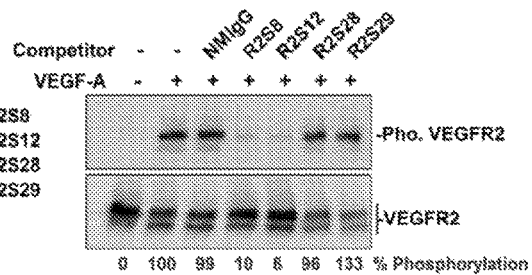

Anti-VEGFR2 scFvs Antagonized the VEGF-A/VEGFR2 Interaction and VEGF-A-induced VEGFR2 Phosphorylation To determine whether the anti-VEGFR2 scFvs can block VEGF-A binding to VEGFR2, we performed a plate-based competition binding assay in which increasing concentrations of scFvs competed with VEGF-A for binding to the immobilized VEGFR2. The interaction of VEGF-A with VEGFR2 was strongly suppressed by R2S8 and R2S12, with half-maximal inhibitory concentrations ($IC_{50}$) of 7.03 and 3.26 nM, respectively, whereas R2S28 and R2S29 exhibited comparatively weak competitive ability (FIG. 2A). We next investigated whether the scFvs could antagonize VEGF-A-mediated activation of VEGFR2 in HUVECs; R2S8 and R2S12 apparently inhibited tyrosine phosphorylation of VEGFR2 by VEGF-A, and R2S12 exhibited the strongest inhibition activity (FIG. 2B).

Identification of Binding Epilopes of Anti-VEGFR2 scFv

To map the binding domain responsible for anti-VEGFR2 scFv, we generated a series of VEGFR2 deletion mutants, which consist of signal peptide and transmembrane domain (FIG. 8). These protein mutants were ectopically expressed in 293T cells, and examined by immunofluorescent staining with R2S8, R2S12, and R2S28 (Table 2). We found that R2S28 bound to cells expressing VEGFR2(1-7), but not to cells expressing VEGFR2(2-7) or VEGFR2(4-7), suggesting that domain 1 of VEGFR2 is necessary for R2S28 binding. R2S8 and R2S12 bound to 293T cells expressing VEGFR2 (1-7) and VEGFR2(2-7), but not to cells expressing constructs lacking domain 3, e.g., VEGFR2(4-7), VEGFR2 (del2-3), or VEGFR2(del3), further indicating that their binding epitopes are located within domain 3. Table 2 shows epitope mapping of anti-VEGFR2 scFv.

TABLE 2

| | R2S8 | R2S12 | R2S28 |
|---|---|---|---|
| VEGFR2(1-7) | + | + | + |
| VEGFR2(2-7) | + | + | − |
| VEGFR2(3-7) | nd* | nd* | nd* |
| VEGFR2(4-7) | − | − | − |
| VEGFR2(del2-3) | − | − | + |
| VEGFR2(del3) | − | − | + |
| VEGFR2(M1) | − | − | + |
| VEGFR2(M2) | + | + | + |

*nd, binding not determined because the construct was not expressed.

Figure 2C:
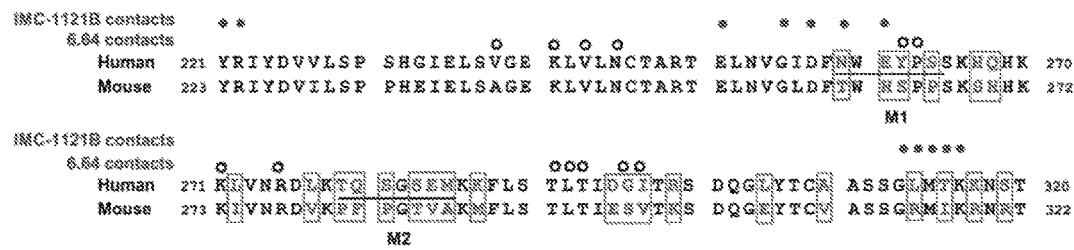

Furthermore, we found that both neutralizing scFvs, R2S8 and R2S12, did not cross-react with murine VEGFR2 protein. Amino acid sequence alignment between human and murine VEGFR2 revealed that domain 3, which has only 67% identity, is the most diverse of the seven domains of the extracellular region of VEGFR2. Thus, we speculated that the distinct epitopes of R2S8 and R2S12 in domain 3 of human VEGFR2 are not displayed in murine VEGFR2. Comparing domain 3 of human and mouse revealed that thirty residues are different, and that these residues are grouped into clusters. To identify the amino acid residues in domain 3 critical for R2S8 and R2S12 binding, we selected two major clusters (M1 and M2) for mutagenesis, as follows: the human NWEYPS (SEQ ID NO: 66) and TQSGSEM (SEQ ID NO: 67) residues were substituted with mouse TWHSPP (SEQ ID NO: 68) and PFPGTVA (SEQ ID) NO: 69) residues, respectively (FIG. 2C). The results of immunofluorescent staining show that R2S8 and R2S12 do not recognize 293T cells expressing VEGFR2-M1 mutant protein. In contrast, mutations in the M2 region of VEGFR2 had no effect on binding to R2S8 and R2S12 (Table 2).

Figure 2D:
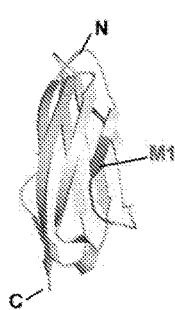
Figure 2E:
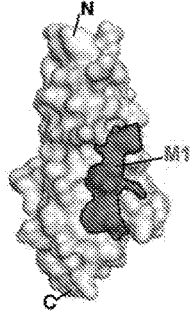
Figure 2F:
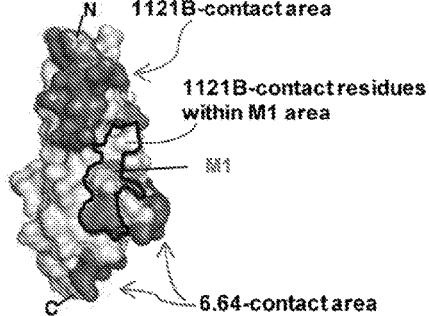
Figure 4A:
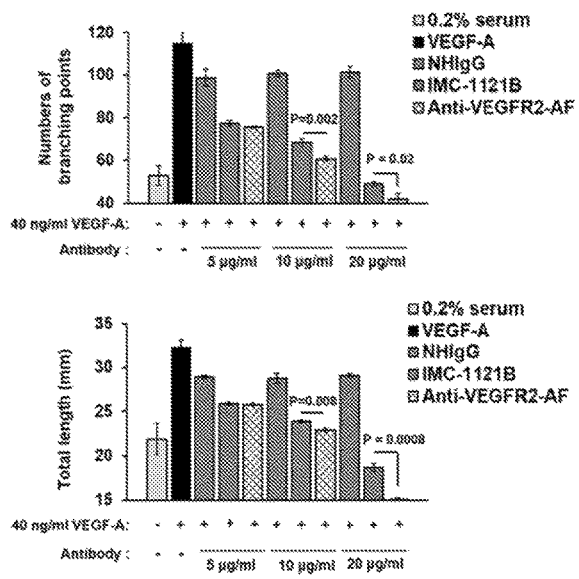
FIGS. 4A-B show that anti-VEGFR2-AF hAb inhibits the VEGFR2 signaling pathway and disrupts capillary structure formation in HUVECs. (A) Capillary structure formation assays were performed using MATRIGEL®-coated μ-Slides. HUVECs ($4 \times 10^4$ cells per well) were incubated with 0.2% FBS and treated with 40 ng/ml VEGF-A, or 40 ng/ml VEGF-A together with NHIgG. IMC-1121B, or anti-VEGFR2-AF antibody for 5 hours at 37° C. Tubular structures were observed under phase contrast, and the relative sprout length (lower panel) and branching points (upper panel) were quantitatively measured with ImageJ software. All data were obtained from three independent experiments. (B) HUVECs were treated with 50 ng VEGF-A or 100 nM anti-VEGFR2-AF or IMC-1121B for 10 min at 37° C. Total protein was prepared from treated HUVECs and examined by Western blot analysis. α-tubulin was used as a loading control.
Figure 4B:
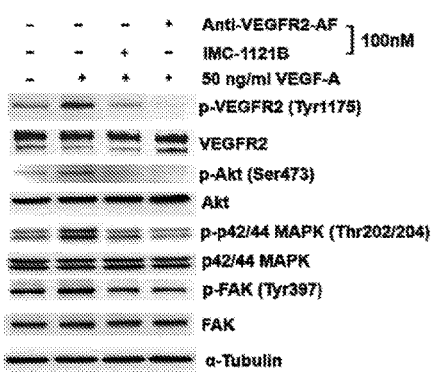
Figure 5A:
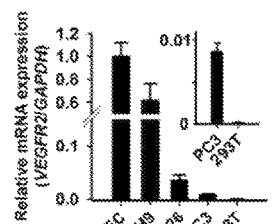
FIGS. 5A-F show characterization of VEGFR2 activity in human prostate cancer cells. (A) Analysis of VEGFR2 expression in the indicated cell lines by quantitative RT-PCR. 293T cells were used as a negative control. Expression of VEGFR2 was normalized to that of GAPDH. (B) PC-3 cells treated with VEGF-A were subjected to colony formation, MTT, and invasion assays. n=6 in each group. (C) PC-3 cells were treated with VEGFR2-targeted shRNA (shVEGFR2), and VEGFR2 expression was analyzed by quantitative RT-PCR. Luciferase shRNA (shLuc) was used as a negative control. (D) MTT, colony formation, and Transwell invasion assays were performed to analyze shVEGFR2-PC-3 cells treated with VEGF-A. (E) Box plots showing relative VEGFR2 expression in metastatic prostate tumors as compared with benign and primary tumors, as determined using a public microarray database. (F) Immunohistochemical staining of a human prostate cancer tissue array (PRC481, Pantomics) using anti-VEGFR2 antibody (55B11, Cell Signaling) to analyze VEGFR2 protein expression in human normal and tumor prostate tissues.
Figure 5B:
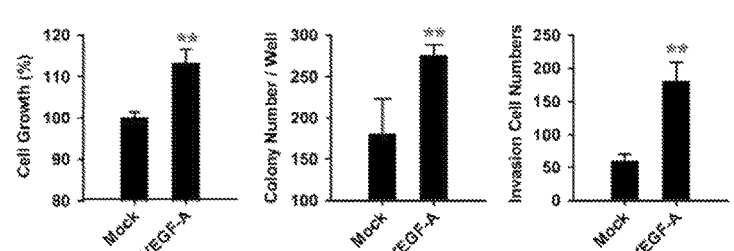
Figure 5C:
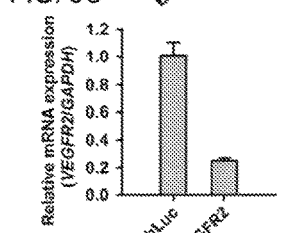
Figure 5D:
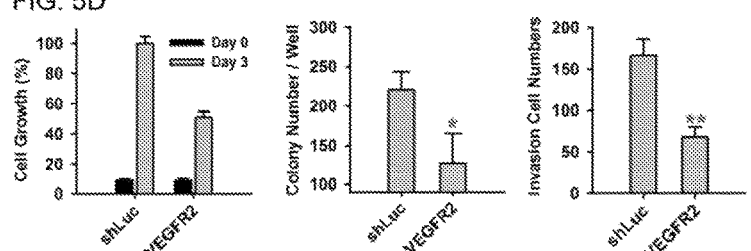
Figure 5E:
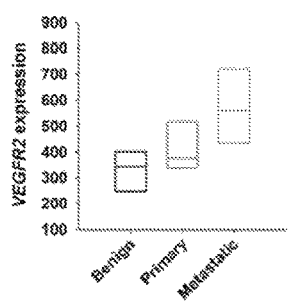
Figure 5F:
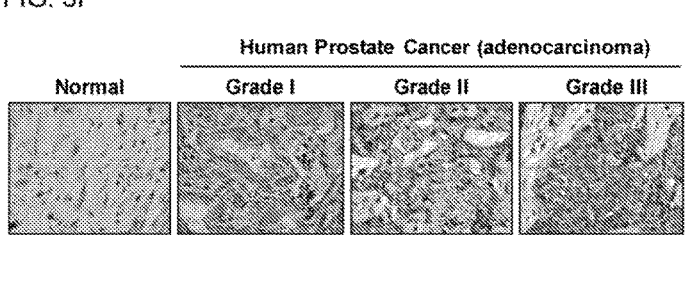

We built a molecular model of VEGFR2 domain 3 from previously reported crystal structural information and our mutagenesis data. The ribbon and surface models show that the NWEYPS (SEQ ID NO: 66) residues (M1 region) localize to a β-strand and middle surface of VEGFR2 domain 3 (FIGS. 2D and 2E). The contacting residues and binding surface of the neutralizing anti-VEGFR2 antibodies, IMC-1121B and 6.64, are located on VEGFR2 domain 3 (FIGS. 2C and 2F). We observed that the M1 region is close to the binding epitopes of the IMC-121B and 6.64 antibodies. Two binding residues, Asn259 and Glu261, of IMC-1121B antibody were found to be situated in the M1 region. Therefore, our results suggest that the binding epitopes of R2S8 and R2S12 are most likely different from those of IMC-1121B and 6.64 antibodies.

Affinity Maturation of R2S12 was Performed to Generate an Anti-VEGFR2-AF Human Antibody with Higher Binding Activity Neutralizing antibodies with high affinity are important for therapeutic efficacy. As R2S12 was demonstrated to exhibit the greatest binding and antagonizing activity of the examined scFvs, we further improved its binding activity using phage display-based affinity maturation. After four rounds of stringent in vitro selection, a clone (R2S12AF) with superior binding activity was identified (FIGS. 9A-B). Four residues within $V_L$-CDR3 of R2S12-AF are different from its parental clone, R2S12 (FIG. 3A). The scFv format has been shown to be of limited clinical use on account of their short serum half-life (approximately 3.5 hours) and inability to trigger human effector functions. To overcome these challenges, we molecularly engineered the coding sequences of R2S12 and R2S12-AF scFv into a human IgG1 backbone to create anti-VEGFR2 and anti-VEGFR2-AF fully human antibody (hAb), respectively.

We analyzed the affinity of both human antibodies to VEGFR2 using a BIACORE T100™. Measurement of the kinetic parameters of antibody-antigen showed that anti-VEGFR2-AF hAb possesses a sub-nmol/L affinity constant ($K_d$=0.264 nM) and an 8-fold increase in binding affinity to VEGFR2 over its parental clone anti-VEGFR2 hAb ($K_d$=2.1 nM; FIG. 3B). We performed solid-phase competitive assays to quantitatively evaluate the disruption of VEGF-A/VEGFR2 binding by individual antibodies. FIG. 3C shows that the $IC_{50}$ value of VEGF-A binding to VEGFR2 was 0.88 nM for anti-VEGFR2-AF hAb, 1.87 nM for anti-VEGFR2 hAb, and 1.42 nM for IMC-1121B. These data indicate that anti-VEGFR2-AF hAb is superior to IMC-1121B at blocking the VEGF/VEGFR2 interaction. The results of FACS analysis of HUVECs further demonstrate that anti-VEGFR2-AF hAb exhibits stronger binding than IMC-1121B to cell-surface VEGFR2 (FIG. 3D).

Anti-VEGFR2-AF hAb Inhibits Activation of the VEGFR2-mediated Signaling Pathway and Disrupts Capillary Structure Formation in HUVECs To elucidate the anti-angiogenic potential of anti-VEGFR2-AF hAb, we analyzed the impact of anti-VEGFR2-AF hAb on HUVEC growth, migration, and tube formation. We found that anti-VEGFR2-AF hAb suppressed VEGF-A-induced HUVEC proliferation and migration using MTT and wound-healing assays, respectively. To investigate the effect of anti-VEGFR2-AF hAb on endothelial cell tube formation (a critical step in angiogenesis), we examined HUVECs on MATRIGEL® layers in the absence or presence of VEGF-A with anti-VEGFR2-AF hAb (FIG. 4A). The ability of endothelial cells to migrate and organize into capillary-like structures was assessed and quantified using an inverted photomicroscope. We verified that anti-VEGFR2-AF hAb is more effective than IMC-1121B in suppressing VEGF-A-triggered capillary-like structures, based on measurements of tubule length and branch point number (FIG. 4A).

To investigate the molecular mechanism underlying the anti-angiogenic properties of anti-VEGFR2-AF hAb, we examined the signaling molecules and pathways by Western blotting (FIG. 4B). We found that anti-VEGFR2-AF hAb efficiently diminished VEGF-A-induced phosphorylation of VEGFR-2 and their downstream signaling molecules, such as Akt, MAPK, and FAK. In particular, the levels of phosphorylated VEGFR2, Akt, and MAPK in the anti-VEGFR2-AF-treated group were lower than those in IMC-1121B-treated group, whereas FAK phosphorylation was only marginally reduced by treatment with either antibody (FIG. 4B). The results indicate that anti-VEGFR2-AF hAb significantly inhibits several essential steps of vascular endothelial cell angiogenesis, suggesting that this antibody may have anti-angiogenic potential in vivo.

Anti-VEGFR2-AF hAb Inhibits VEGF-A-induced Cellular Function in VEGFR2-expressing Human Prostate Cancer Cells We chose the human prostate cancer cell line PC-3 as a model to study the therapeutic efficacy of anti-VEGFR2-AF hAb in inhibiting tumor growth. We performed quantitative reverse transcription-PCR (qRT-PCR) analysis to investigate the endogenous expression of VEGFR2 in PC-3 cells (FIG. 5A). HUVECs, EA.hy926, and hESC-H9 cells are known to exhibit high expression of VEGFR2 mRNA, and were thus used as positive controls. We found that VEGFR2 mRNA was readily detectable in PC-3 cells, but was barely detectable in negative control 293T cells.

To characterize the functional significance of VEGF-A/VEGFR2 on PC-3 cells, we analyzed PC-3 cell activity upon VEGF-A treatment. We found that treatment with VEGF-A was able to enhance various cellular activities of PC-3 cells, including proliferation, colony formation, and invasive ability (FIG. 5B). We established VEGFR2-knock down PC-3 cells with lentivirus-mediated shRNA (shVEGFR2; FIG. 5C), and found that knockdown of VEGFR2 reduced proliferation, colony formation, and invasive ability of PC-3 cells as compared to PC-3 cells infected with control shRNA (shLuc; FIG. 5D). We treated PC-3 cells with anti-VEGFR2-AF hAb and demonstrated that VEGF-A-induced cellular activities can be suppressed by anti-VEGFR2-AF hAb (FIGS. 10A-C). Hence, these data show that the VEGF/VEGFR2 axis is crucial for clonogenic and tumorigenic capabilities of PC-3 cells.

We investigated VEGFR2 expression patterns in relevant microarray data sets which are publicly available. We found that the amount of VEGFR2 transcripts in metastatic prostate tumor was higher than that in primary tumor (FIG. 5E). We used a commercial anti-VEGFR2 antibody to stain a human prostate cancer tissue array, and revealed that VEGFR2 is detectable in tumor cells, and that its expression level is elevated in Grade III prostate adenocarcinoma as compared to Grade I (FIG. 5F). In normal prostate tissue specimens, VEGFR2 is present in vascular endothelium, but not in normal prostate cells.

Therapeutic Efficacy of Anti-VEGFR2-AF in Human Prostate Cancer Xenografts

Figure 6A:
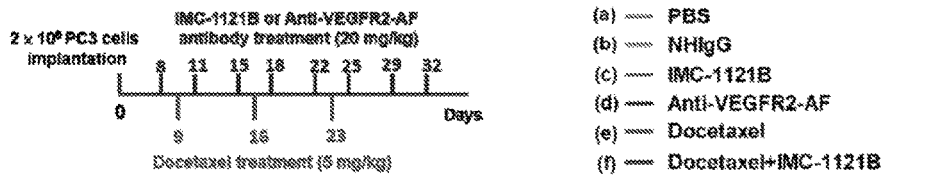
FIGS. 6A-E show analysis of the therapeutic efficacy of anti-VEGFR2-AF hAb in a PC-3 mouse xenograft model. (A) The treatment schedule. (B) The tumor growth profiles of mice of each group. (C) Body weight of each group. (D) At the end of the treatment period, tumor mass was dissected from each mouse. (E) Tumor weight was measured at the end of the treatment period. All data are shown as the mean of nine mice per group; bars, SE; *, P<0.05.
Figure 6B:
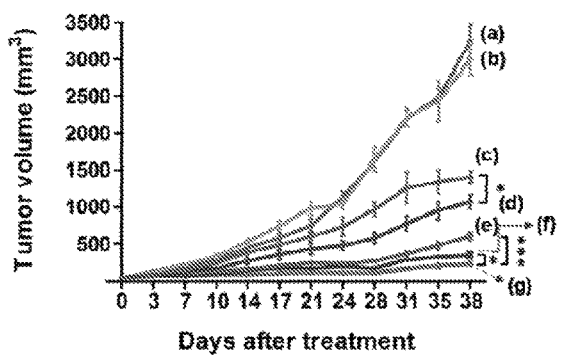
Figure 6C:
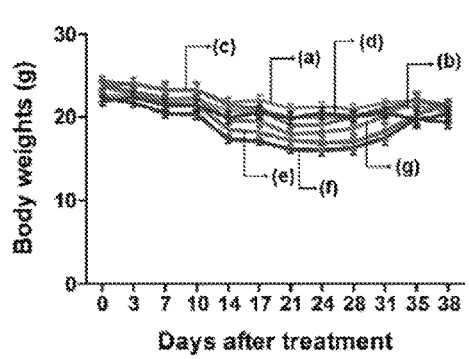

We used the PC-3 xenografl prostate tumor model to elucidate the in vivo antitumor activity of anti-VEGFR2-AF hAb versus IMC-1121B, Docetaxel is a first-line chemotherapeutic agent for patients with metastatic castration-resistant prostate cancer. Thus, we also investigated the therapeutic effects of combining docetaxel and anti-VEGFR2-AF hAb or IMC-1121B. NOD/SCID mice bearing PC-3 xenografts were administrated with IMC-1121B, anti-VEGFR2-AF hAb, docetaxel, anti-VEGFR2-AF hAb plus docetaxel, sir IMC-1121B plus docetaxel (FIG. 6A). By day 38, tumor growth reduction reached 90% for mice treated with the combination of anti-VEGFR2-AF hAb plus docetaxel, 82% for mice treated with the combination of IMC-1121B plus docetaxel, 70% for mice treated with docetaxel, 52% for mice treated with anti-VEGFR2-AF hAb, and 45% for mice treated with IMC-1121B (FIG. 6B). Body weight was used as a surrogate indicator of the health status of the mice (FIG. 6C). The anti-VEGFR2-AF hAb and IMC-1121B groups exhibited no significant changes in body weight during the treatment period as compared to the NHIgG group. Treatment with docetaxel alone caused a marked loss of body weight (about 20%). Mice treated with docetaxel in combination with other antibodies lost a similar amount of body weight to mice treated with docetaxel alone, which indicates that anti-VEGFR2-AF hAb and IMC-1121B do not enhance docetaxel-induced toxicity.

Figure 6D:
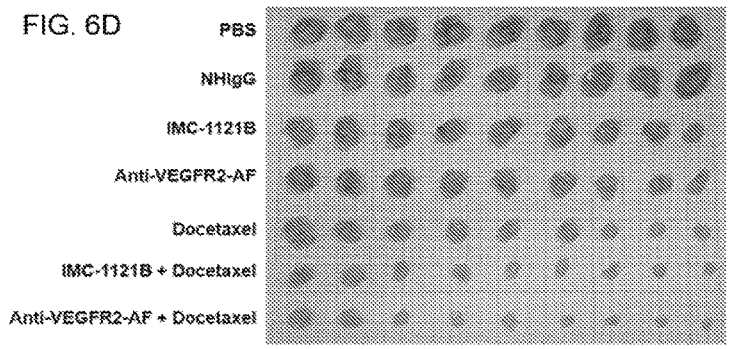
Figure 6E:
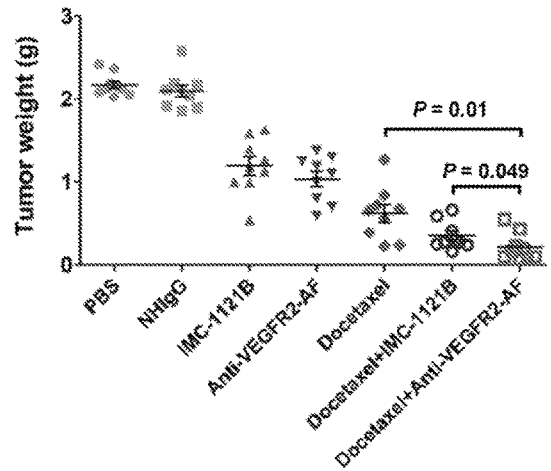

Tumor weights were measured and found to be consistent with tumor volume (FIGS. 6D and 6E). We further examined tumor tissues in each group by using anti-CD31 antibody to detect tumor blood vessels and TUNEL assay to identify apoptotic cells. We found that anti-VEGFR2-AF hAb is superior to IMC-1121B at reducing tumor vascular density and enhancing cancer cell apoptosis (FIGS. 11A and 11B). These results show that anti-VEGFR2-AF hAb is more effective than IMC-1121B at attenuating tumor growth, and that anti-VEGFR2-AF hAb significantly enhances the effectiveness of docetaxel in the treatment of human prostate tumors in mice.

Figure 7A:
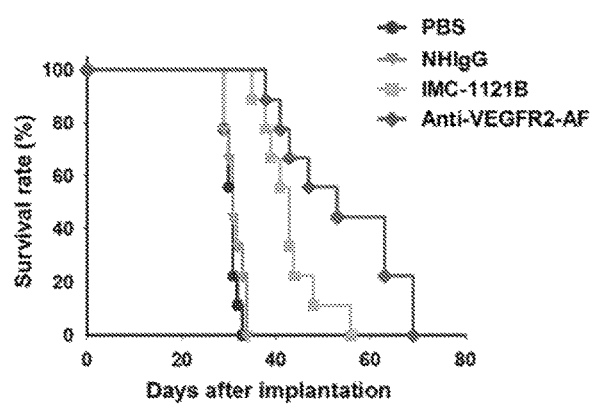
FIGS. 7A-E show that anti-VEGFR2-AF hAb exhibits greater antitumor activity than IMC-1121B in a HL60 mouse xenograft model. (A) Kaplan-Meier survival analysis of mice of each group. Survival was significantly prolonged in the anti-VEGFR2-AF hAb group compared with the IMC-1121B group based on log-rank test (P=0.0284). (B) Body weight of mice of each group. (C) Ovaries were dissected from each mouse after death. The ovaries from a NSG mouse without leukemia were used as a normal control. (D) Ovary volume in mice treated with IMC-1121B or anti-VEGFR2-AF. (E) Morphometric analysis of lymph node (LN) changes in leukemia-tumor bearing mice. Leukemia cells that had metastasized to lymph nodes were dissected from mice of the indicated groups (n=9 for each group).
Figure 7B:
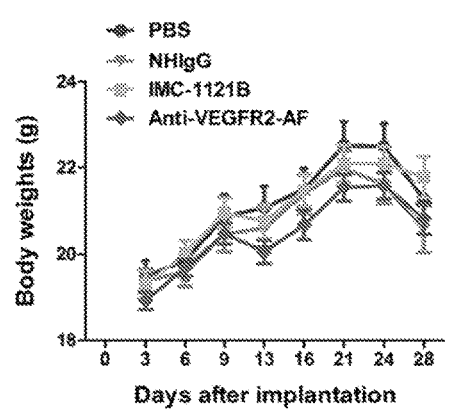

Anti-VEGFR2-AF hAlb Prolonged the Survival of Mice Bearing HL-60 Leukemia Xenografts The VEGF-A/VEGFR2 pathway has crucial functions not only in solid tumors, but also in liquid tumors, such as leukemia or lymphoma. Previous studies provided evidence that IMC-1121B inhibits HL-60 leukemia growth, and prolongs survive in a mouse model. To compare the anti-leukemia effect of IMC-1121B with that of anti-VEGFR2-AF hAb, we developed a HL-60 leukemia xenograft model in NSG mice. Mice received intravenous injections of $5 \times 10^6$ HL-60 cells, and were treated 3 days later with IMC-1121B, anti-VEGFR2-AF, NHIgG, or PBS. As shown in FIG. 7A, all PBS- or NHIgG-treated mice died within 36 days; however, leukemia-bearing mice treated with antibodies against VEGFR2 exhibited a marked extension in survival time. Mice treated with anti-VEGFR2-AF hAb survived longer (70 days; median=53 days) than those treated with IMC-1121B (56 days; median=43 days). No significant changes in body weight were observed between groups (FIG. 7B).

Figure 12A:
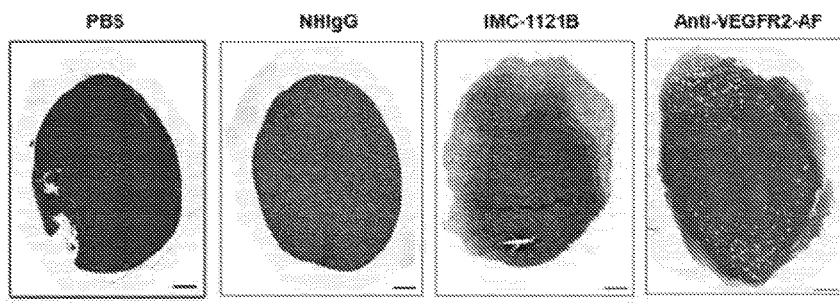
FIGS. 12A-B show histopathological phenotype of ovaries of human leukemia xenograft mice following antibody treatment. Ovaries were harvested from HL-60 tumor-bearing mice after treatment with saline, NHIgG, IMC-1121B, or anti-VEGFR2-AF hAb. The tissues were sliced and stained with hematoxylin and eosin (H&E), revealing infiltration with leukemia cells. The group treated with Anti-VEGFR2-AF showed fewer blood vessels, and retained some primary oocytes. n=9 in each group. (A) Ovary at 200× magnification. Scale bar, 500 μm. (B) Scale bar, 150 μm.
Figure 12B:
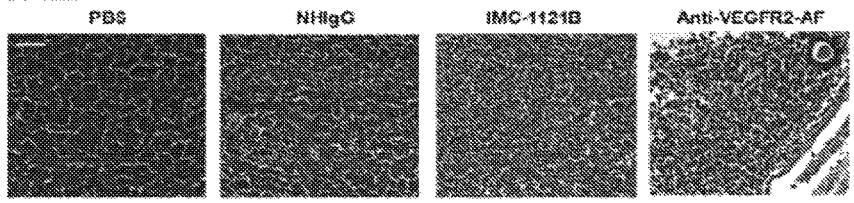
Figure 7C:
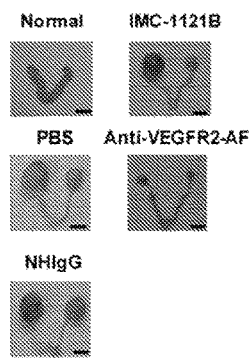
Figure 7D:
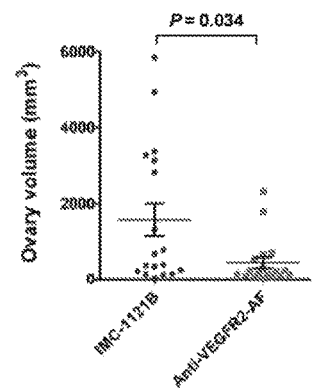

Post-mortem histopathological examinations of all mice showed that no obvious pathological changes were found in the livers, spleens, heart, or kidneys of mice in each group. The ovaries of leukemia-bearing mice were swollen as compared to normal ovaries (FIG. 7C). H&E staining revealed that the ovaries had been infiltrated by metastatic leukemia cells (FIGS. 12A and 12B). The average ovarian volume in the anti-VEGFR2-AF hAb-treated group was significantly smaller than that in the IMC-1121B-treated group (FIG. 7D).

Figure 7E:
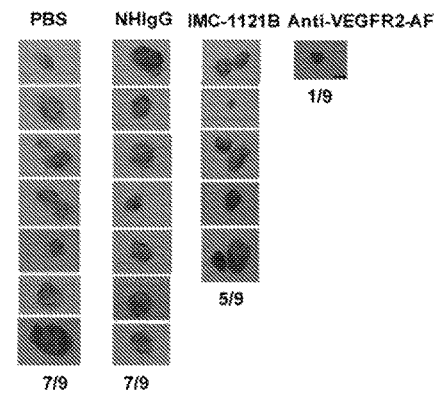
Figure 10A:
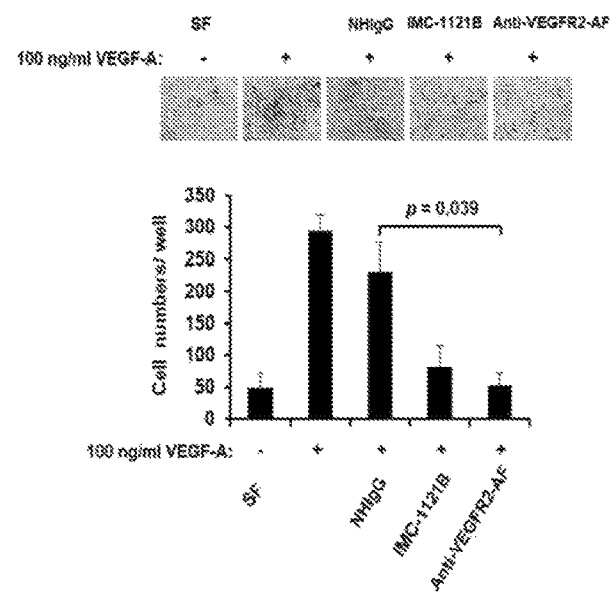
FIGS. 10A-C show that anti-VEGFR2-AF hAb antagonized VEGF-A mediated cellular activity in PC-3 cells. (A) Transwell assays were carried out to examine the invasion capacity of PC-3 cells subjected to the indicated treatments. Upper panel: Giemsa staining of invasive cells. 100× magnification; n=3 in each group; scale bar, 150 μm. (B) A total of 1×10 PC-3 cells were seeded in a six-well plate, and treated with or without 100 ng/ml VEGF-A and 10 μg/ml of NHIgG IMC-1121B. or anti-VEGFR2-AF antibody. The plate was incubated for 7 days to allow colony formation. Cell colonies were visualized by crystal violet staining. The relative number of colonies was calculated in each well after elution of crystal violet solution. n=3 in each group. (C) Wound healing assay. PC-3 cells were incubated in RPMI with 2% FBS, and stimulated by treatment with 100 ng/ml VEGF-A in the presence or absence of 10 μg/ml NHIgG IMC-1121B, or anti-VEGFR2-AF, individually. Images were taken after 0, 16, and 36 hours of incubation. Scale bar, 150 μm. n=3 in each group. Error bar, SE.
Figure 10B:
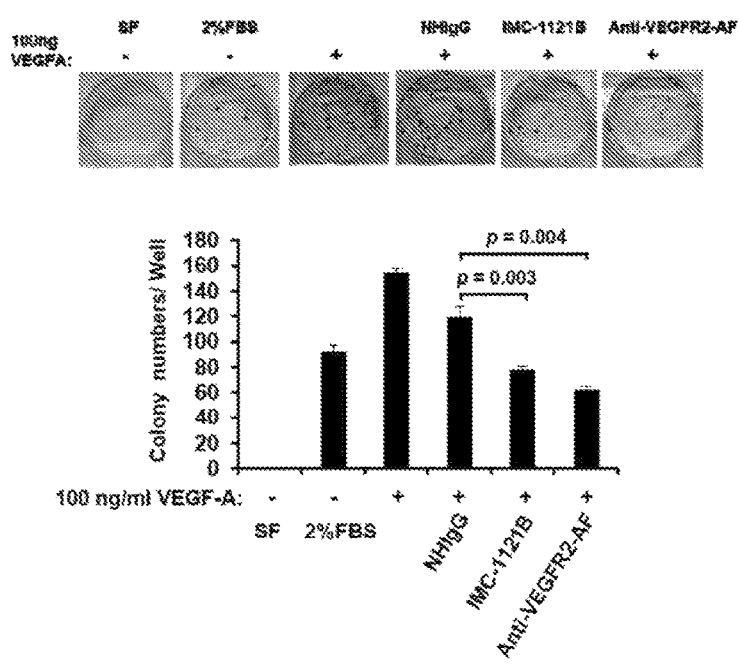
Figure 10C:
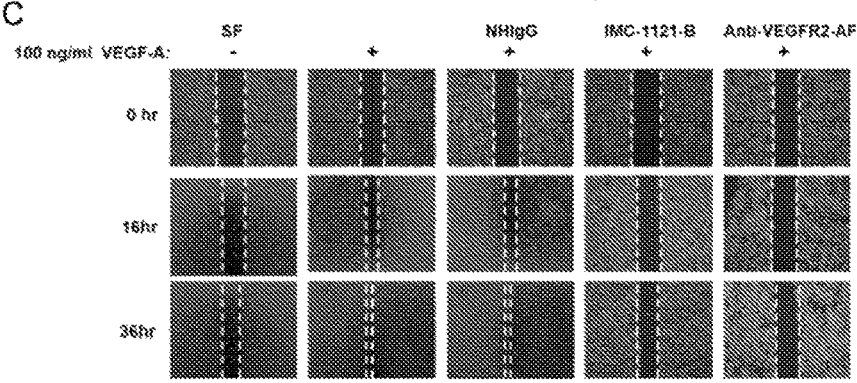

Furthermore, lymph nodes with leukemia infiltration were identified in one of nine mice treated with anti-VEGFR2-AF hAb, whereas lymph nodes with leukemia infiltration were present in five of nine mice treated with IMC-1121B (FIG. 7E).

Anti-VEGFR2-AF hAb-mediated targeting of VEGFR2 on tumor endothelium not only disrupts VEGF-A-induced signaling, but also triggers antibody-dependent cell-mediated cytotoxicity (ADCC) or complement-dependent cytotoxicity (CDC) to directly kill the targeted cells, which may enhance current anti-angiogenesis therapy.

Anti-VEGFR2-AF hAb may be able to exert dual targeting and inhibition effects on both tumor vascular and malignant cells, as tumor cells also express VEGFR2. The dual targeting ability may have synergistic effects on cancer therapy. We produced a fully human antibody, anti-VEGFR2-AF, which exhibited superior binding to VEGFR2, antagonizing the activity of this receptor. Similar to IMC-1121B, anti-VEGFR2-AF hAb specifically bound to human VEGFR2, but not to murine VEGFR2. Compared to IMC-1121B, anti-VEGFR2-AF hAb presented with greater antitumor efficacy in vitro and in vivo, by interrupting VEGF-A/VEGFR2 axis-mediated signaling. We are the first to demonstrate that anti-VEGFR2 antibody can enhance the therapeutic efficacy of docetaxel in the treatment of prostate cancer. The findings suggest that anti-VEGFR2-AF hAb may be potentially used as a therapeutic antibody for cancer treatment by simultaneously and directly inhibiting angiogenesis and VEGFR2-expressing tumor cells.

In summary, compared to FDA-approved anti-VEGFR2 human antibody IMC-1121B (Ramucirumab), anti-VEGFR2-AF hAb possessed significantly superior activity, and suppressed VEGF-A-mediated capillary structure formation in vitro. We observed VEGFR2 expression in human prostate cancer cell line (PC-3) and leukemia cell line (HL-60), and demonstrated that VEGFR2 expression is associated with malignancy and metastasis of human prostate cancer. In PC-3-derived xenograft mouse models, treatment with anti-VEGFR2-AF hAb (monotherapy or combined with docetaxel) suppressed tumor growth and angiogenesis more effectively than treatment with IMC-1121B. In mice with HL-60-derived leukemia, anti-VEGFR2-AF hAb exhibited more significant efficacy than IMC-1121B in prolonging survival and reducing metastasis of leukemia cells to ovaries and lymph nodes.

The foregoing description of the exemplary embodiments of the invention has been presented only for the purposes of illustration and description and is not intended to be exhaustive or to limit the invention to the precise forms disclosed. Many modifications and variations are possible in light of the above teaching. All references cited and discussed in this specification are incorporated herein by reference in their entireties and to the same extent as if each reference was individually incorporated by reference.

What is claimed is:

1. An isolated antibody or an antigen-binding fragment thereof, which comprises a heavy chain variable region ($V_H$) and a light chain variable region ($V_L$), the $V_H$ comprising $V_H$ CDR1, $V_H$ CDR2, and $V_H$ CDR3, and the $V_L$ comprising $V_L$ CDR1, $V_L$ CDR2, and $V_L$ CDR3, wherein:
the $V_H$ CDR1, $V_H$ CDR2, $V_H$ CDR3 comprise the amino acid sequence of SEQ NO: 6, SEQ ID NO: 7, and SEQ ID NO: 8, respectively; and the $V_L$ CDR1, $V_L$ CDR2, and $V_L$ CDR3 comprise the amino acid sequence of SEQ ID NO: 9, Asp Ala Ser, and SEQ ID NO: 10 or 73, respectively.

2. The antibody or antigen-binding fragment thereof of claim 1, wherein:
the $V_L$ CDR3 comprises the amino acid sequence of SEQ ID NO: 73.

3. The antibody or antigen-binding fragment thereof of claim 1, wherein
the $V_H$ comprises the amino acid sequence of SEQ ID NO: 76; and
the $V_L$ comprises the amino acid sequence of SEQ ID NO: 77 or 78.

4. The antibody or antigen-binding fragment thereof of claim 1, which is a single-chain variable fragment, a Fab fragment or a Fv fragment.

5. The antibody or antigen-binding fragment thereof of claim 1, wherein the antibody is a fully human antibody.

6. A composition comprising a therapeutically effective amount of the antibody or antigen-binding fragment thereof of claim 5 and a pharmaceutically acceptable vehicle or carrier.

7. The composition of claim 6, further comprising a therapeutically effective amount of a chemotherapeutic agent.

8. The antibody or antigen-binding fragment thereof of claim 3, wherein the antibody is a fully human antibody.

9. The antibody or antigen-binding fragment thereof of claim 4, wherein the antibody is a fully human antibody.

10. The antibody or antigen-binding fragment thereof of claim 2, wherein the antibody is a fully human antibody.

11. An isolated antibody or an antigen-binding fragment thereof, or a single-chain variable fragment, which comprises:
(a) a heavy chain variable region ($V_H$) comprising the amino acid sequence of SEQ ID NO: 76; and
(b) a light chain variable region ($V_L$) comprising the amino acid sequence of SEQ ID NO: 77 or 78.

12. A method of detecting the presence of VEGFR2 on tumor vascular endothelial cells or cancer cells in a biological sample, comprising:
(i) admixing the antibody or antigen-binding fragment thereof of claim 1 with the biological sample;
(ii) allowing the antibody or antigen-binding fragment thereof and the VEGFR2 on the tumor vascular endothelial cells or cancer cells in the biological sample to interact and form a complex; and
(iii) detecting the presence of the VEGFR2 on the tumor vascular endothelial cells or cancer cells in the complex.

13. A method of detecting the presence of VEGFR2 on tumor vascular endothelial cells or cancer cells in a biological sample, comprising:
(i) admixing the antibody or antigen-binding fragment thereof of claim 2 with the biological sample;
(ii) allowing the antibody or antigen-binding fragment thereof and the VEGFR2 on the tumor vascular endothelia cells or cancer cells in the biological sample to interact and from a complex; and
(iii) detecting the presence of the VEGFR2 on the tumor vascular endothelial cells or cancer cells in the complex.

14. A method for inhibiting tumor growth, tumor angiogenesis, and/or inducing cytotoxicity in cancer cells, comprising:
administering to a subject in need thereof a composition comprising a therapeutically effective amount of the isolated antibody or antigen-binding fragment thereof of claim 1 and a pharmaceutically acceptable carrier, wherein the tumor and/or cancer cell expresses VEGFR2.

15. A method for inhibiting tumor growth, tumor angiogenesis, and/or inducing cancer cell cytotoxicity in a subject in need thereof, comprising:
  administering to the subject in need thereof a therapeutically effective amount of the antibody or antigen-binding fragment thereof of claim 2, wherein the antibody is a fully human antibody.

16. The method of claim 15, wherein the tumor or cancer is at least one selected from the group consisting of pancreatic, breast, lung, leukemia, prostate and ovary cancer.

17. A method for inhibiting tumor growth, tumor angiogenesis, and/or inducing cancer cell cytotoxicity in a subject in need thereof, comprising:
  administering to the subject in need thereof a therapeutically effective amount of the antibody or antigen-binding fragment thereof of claim 5.

18. The method of claim 17, wherein the tumor or cancer is at least one selected from the group consisting of pancreatic, breast, lung, leukemia, prostate and ovary cancer.

19. A method for inhibiting tumor growth, tumor angiogenesis, and/or inducing cancer cell cytotoxicity in a subject in need thereof, comprising:
  administering to the subject in need thereof a therapeutically effective amount of the antibody or antigen-binding fragment thereof of claim 8.

20. The method of claim 19, wherein the tumor or cancer is at least one selected from the group consisting of pancreatic, breast, lung, leukemia, prostate and ovary cancer.

* * * * *

SEQUENCE LISTING

```
<160> NUMBER OF SEQ ID NOS: 80

<210> SEQ ID NO 1
<211> LENGTH: 8
<212> TYPE: PRT
<213> ORGANISM: Artificial Sequence
<220> FEATURE:
<223> OTHER INFORMATION: R2PC8 VH CDR1

<400> SEQUENCE: 1

Gly Phe Thr Phe Ser Ser Tyr Ser
1               5

<210> SEQ ID NO 2
<211> LENGTH: 8
<212> TYPE: PRT
<213> ORGANISM: Artificial Sequence
<220> FEATURE:
<223> OTHER INFORMATION: R2PC8 VH CDR2

<400> SEQUENCE: 2

Ile Ser Ser Ser Ser Ser Tyr Ile
1               5

<210> SEQ ID NO 3
<211> LENGTH: 9
<212> TYPE: PRT
<213> ORGANISM: Artificial Sequence
<220> FEATURE:
<223> OTHER INFORMATION: R2PC8 VH CDR3

<400> SEQUENCE: 3

Ala Arg Ser Thr Asp Ala Phe Asp Ile
1               5

<210> SEQ ID NO 4
<211> LENGTH: 6
<212> TYPE: PRT
<213> ORGANISM: Artificial Sequence
<220> FEATURE:
<223> OTHER INFORMATION: R2PC8 VL CDR1

<400> SEQUENCE: 4

Gln Arg Ile Ser Asn Tyr
1               5

<210> SEQ ID NO 5
<211> LENGTH: 9
<212> TYPE: PRT
<213> ORGANISM: Artificial Sequence
<220> FEATURE:
<223> OTHER INFORMATION: R2PC8 V L CDR3

<400> SEQUENCE: 5

Gln Gln Tyr Asp Arg Tyr Pro Pro Thr
1               5

<210> SEQ ID NO 6
<211> LENGTH: 8
<212> TYPE: PRT
<213> ORGANISM: Artificial Sequence
<220> FEATURE:
<223> OTHER INFORMATION: R2PC12 VH CDR1

<400> SEQUENCE: 6

Gly Phe Thr Phe Gly Ser Tyr Thr
1               5
```

```
<210> SEQ ID NO 7
<211> LENGTH: 8
<212> TYPE: PRT
<213> ORGANISM: Artificial Sequence
<220> FEATURE:
<223> OTHER INFORMATION: R2PC12VH CDR2

<400> SEQUENCE: 7

Ile Thr Ser Gly Ser Ser Tyr Ile
1               5

<210> SEQ ID NO 8
<211> LENGTH: 10
<212> TYPE: PRT
<213> ORGANISM: Artificial Sequence
<220> FEATURE:
<223> OTHER INFORMATION: R2PC12 VH CDR3

<400> SEQUENCE: 8

Ala Arg Gly Ser Ala Ser Ala Phe Asp Ile
1               5                   10

<210> SEQ ID NO 9
<211> LENGTH: 6
<212> TYPE: PRT
<213> ORGANISM: Artificial Sequence
<220> FEATURE:
<223> OTHER INFORMATION: R2PC12 VL CDR1

<400> SEQUENCE: 9

Asp Asp Ile Ile Asn Tyr
1               5

<210> SEQ ID NO 10
<211> LENGTH: 9
<212> TYPE: PRT
<213> ORGANISM: Artificial Sequence
<220> FEATURE:
<223> OTHER INFORMATION: R2PC12 V L CDR3

<400> SEQUENCE: 10

Gln Gln Tyr Asp Ile Leu Pro Leu Thr
1               5

<210> SEQ ID NO 11
<211> LENGTH: 8
<212> TYPE: PRT
<213> ORGANISM: Artificial Sequence
<220> FEATURE:
<223> OTHER INFORMATION: R2PC28 VH CDR1

<400> SEQUENCE: 11

Glu Phe Thr Phe Ser His Tyr Asn
1               5

<210> SEQ ID NO 12
<211> LENGTH: 8
<212> TYPE: PRT
<213> ORGANISM: Artificial Sequence
<220> FEATURE:
<223> OTHER INFORMATION: R2PC28 VH CDR2

<400> SEQUENCE: 12

Ile Ser Asp Asp Gly Arg Asn Lys
1               5
```

```
<210> SEQ ID NO 13
<211> LENGTH: 14
<212> TYPE: PRT
<213> ORGANISM: Artificial Sequence
<220> FEATURE:
<223> OTHER INFORMATION: R2PC28 VH CDR3

<400> SEQUENCE: 13

Ala Arg Val Pro Thr Val Trp Arg Gly Gly Val Tyr Asp Ile
1               5                   10

<210> SEQ ID NO 14
<211> LENGTH: 6
<212> TYPE: PRT
<213> ORGANISM: Artificial Sequence
<220> FEATURE:
<223> OTHER INFORMATION: R2PC28 VL CDR1

<400> SEQUENCE: 14

Gln Ser Val Gly Ser Tyr
1               5

<210> SEQ ID NO 15
<211> LENGTH: 9
<212> TYPE: PRT
<213> ORGANISM: Artificial Sequence
<220> FEATURE:
<223> OTHER INFORMATION: R2PC28 V L CDR3

<400> SEQUENCE: 15

His Gln Ser Ser Ser Leu Pro Arg Thr
1               5

<210> SEQ ID NO 16
<211> LENGTH: 8
<212> TYPE: PRT
<213> ORGANISM: Artificial Sequence
<220> FEATURE:
<223> OTHER INFORMATION: R2PC29 VH CDR1

<400> SEQUENCE: 16

Gly Gly Asn Phe Ile Ser Lys Gly
1               5

<210> SEQ ID NO 17
<211> LENGTH: 8
<212> TYPE: PRT
<213> ORGANISM: Artificial Sequence
<220> FEATURE:
<223> OTHER INFORMATION: R2PC29 VH CDR2

<400> SEQUENCE: 17

Ile Ile Pro Leu Phe Gly Thr Gly
1               5

<210> SEQ ID NO 18
<211> LENGTH: 16
<212> TYPE: PRT
<213> ORGANISM: Artificial Sequence
<220> FEATURE:
<223> OTHER INFORMATION: R2PC29 VH CDR3

<400> SEQUENCE: 18

Ala Thr Ala Asp Val Asp Tyr Ser Asp Ser Leu Glu Ala Phe Asp Met
1               5                   10                  15
```

```
<210> SEQ ID NO 19
<211> LENGTH: 6
<212> TYPE: PRT
<213> ORGANISM: Artificial Sequence
<220> FEATURE:
<223> OTHER INFORMATION: R2PC29 VL CDR1

<400> SEQUENCE: 19

Gln Ser Ile Asn Asn Tyr
1               5

<210> SEQ ID NO 20
<211> LENGTH: 8
<212> TYPE: PRT
<213> ORGANISM: Artificial Sequence
<220> FEATURE:
<223> OTHER INFORMATION: R2PC29 V L CDR3

<400> SEQUENCE: 20

Gln Gln Ser Tyr Ser Thr Pro Leu
1               5

<210> SEQ ID NO 21
<211> LENGTH: 8
<212> TYPE: PRT
<213> ORGANISM: Artificial Sequence
<220> FEATURE:
<223> OTHER INFORMATION: R2PC45 VH CDR1

<400> SEQUENCE: 21

Gly Phe Thr Phe Ser Ser Tyr Ala
1               5

<210> SEQ ID NO 22
<211> LENGTH: 8
<212> TYPE: PRT
<213> ORGANISM: Artificial Sequence
<220> FEATURE:
<223> OTHER INFORMATION: R2PC45 VH CDR2

<400> SEQUENCE: 22

Ile Ser Tyr Asp Gly Ser Asn Lys
1               5

<210> SEQ ID NO 23
<211> LENGTH: 16
<212> TYPE: PRT
<213> ORGANISM: Artificial Sequence
<220> FEATURE:
<223> OTHER INFORMATION: R2PC45 VH CDR3

<400> SEQUENCE: 23

Ala Arg Glu Gln Asp Tyr Gly Ser Ser Gly Asp Ala Phe Asp Ile
1               5                   10                  15

<210> SEQ ID NO 24
<211> LENGTH: 6
<212> TYPE: PRT
<213> ORGANISM: Artificial Sequence
<220> FEATURE:
<223> OTHER INFORMATION: R2PC45 VL CDR1

<400> SEQUENCE: 24

Gln Arg Ile Ser Ser Tyr
1               5
```

```
<210> SEQ ID NO 25
<211> LENGTH: 9
<212> TYPE: PRT
<213> ORGANISM: Artificial Sequence
<220> FEATURE:
<223> OTHER INFORMATION: R2PC45 V L CDR3

<400> SEQUENCE: 25

His Gln Ser Tyr Ser Ala Pro Pro Thr
1               5

<210> SEQ ID NO 26
<211> LENGTH: 25
<212> TYPE: PRT
<213> ORGANISM: Artificial Sequence
<220> FEATURE:
<223> OTHER INFORMATION: R2PC8 VH FR1

<400> SEQUENCE: 26

Gln Val Gln Leu Val Gln Ser Gly Gly Gly Leu Val Lys Pro Gly Gly
1               5                   10                  15

Ser Leu Arg Leu Ser Cys Ala Ala Ser
            20                  25

<210> SEQ ID NO 27
<211> LENGTH: 17
<212> TYPE: PRT
<213> ORGANISM: Artificial Sequence
<220> FEATURE:
<223> OTHER INFORMATION: R2PC8 VH FR2

<400> SEQUENCE: 27

Met Ser Trp Val Arg Gln Ala Pro Gly Lys Gly Leu Glu Trp Val Ser
1               5                   10                  15

Ser

<210> SEQ ID NO 28
<211> LENGTH: 38
<212> TYPE: PRT
<213> ORGANISM: Artificial Sequence
<220> FEATURE:
<223> OTHER INFORMATION: R2PC8 VH FR3

<400> SEQUENCE: 28

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 29
<211> LENGTH: 11
<212> TYPE: PRT
<213> ORGANISM: Artificial Sequence
<220> FEATURE:
<223> OTHER INFORMATION: R2PC8 VH FR4

<400> SEQUENCE: 29

Trp Gly Gln Gly Thr Met Val Thr Val Ser Ser
1               5                   10

<210> SEQ ID NO 30
<211> LENGTH: 26
<212> TYPE: PRT
```

```
<213> ORGANISM: Artificial Sequence
<220> FEATURE:
<223> OTHER INFORMATION: R2PC8 VL FR1

<400> SEQUENCE: 30

Asp Ile Val Met Thr Gln Ser Pro Ser Leu Ser Ala Ser Val Gly
1               5                   10                  15

Asp Arg Val Thr Ile Thr Cys Arg Ala Ser
            20                  25

<210> SEQ ID NO 31
<211> LENGTH: 17
<212> TYPE: PRT
<213> ORGANISM: Artificial Sequence
<220> FEATURE:
<223> OTHER INFORMATION: R2PC8 VL FR2

<400> SEQUENCE: 31

Leu Asn Trp Tyr Gln His Lys Ser Gly Glu Asp Pro Lys Leu Leu Ile
1               5                   10                  15

Tyr

<210> SEQ ID NO 32
<211> LENGTH: 36
<212> TYPE: PRT
<213> ORGANISM: Artificial Sequence
<220> FEATURE:
<223> OTHER INFORMATION: R2PC8 VL FR3

<400> SEQUENCE: 32

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 33
<211> LENGTH: 10
<212> TYPE: PRT
<213> ORGANISM: Artificial Sequence
<220> FEATURE:
<223> OTHER INFORMATION: R2PC8 VL FR4

<400> SEQUENCE: 33

Phe Gly Gln Gly Thr Lys Leu Glu Ile Lys
1               5                   10

<210> SEQ ID NO 34
<211> LENGTH: 25
<212> TYPE: PRT
<213> ORGANISM: Artificial Sequence
<220> FEATURE:
<223> OTHER INFORMATION: R2PC12 VH FR1

<400> SEQUENCE: 34

Gln Val Asn Leu Arg Glu Ser Gly Gly Gly Leu Val Lys Pro Gly Gly
1               5                   10                  15

Ser Leu Arg Leu Ser Cys Ala Ala Ser
            20                  25

<210> SEQ ID NO 35
<211> LENGTH: 17
<212> TYPE: PRT
```

<213> ORGANISM: Artificial Sequence
<220> FEATURE:
<223> OTHER INFORMATION: R2PC12 VH FR2

<400> SEQUENCE: 35

Met Asn Trp Val Arg Gln Ala Pro Gly Lys Gly Leu Glu Trp Val Ala
1               5                   10                  15
Ser

<210> SEQ ID NO 36
<211> LENGTH: 38
<212> TYPE: PRT
<213> ORGANISM: Artificial Sequence
<220> FEATURE:
<223> OTHER INFORMATION: R2PC12 VH FR3

<400> SEQUENCE: 36

Phe Tyr Thr Asp Ser Val Lys Gly Arg Phe Thr Ile Ser Arg Asp Asn
1               5                   10                  15
Ser Arg Ser Ser Leu Phe Leu Gln Met Asn Ser Leu Arg Ala Glu Asp
            20                  25                  30
Thr Ala Ile Tyr Tyr Cys
        35

<210> SEQ ID NO 37
<211> LENGTH: 11
<212> TYPE: PRT
<213> ORGANISM: Artificial Sequence
<220> FEATURE:
<223> OTHER INFORMATION: R2PC12 VH FR4

<400> SEQUENCE: 37

Trp Gly Gln Gly Thr Met Val Thr Val Ser Ser
1               5                   10

<210> SEQ ID NO 38
<211> LENGTH: 26
<212> TYPE: PRT
<213> ORGANISM: Artificial Sequence
<220> FEATURE:
<223> OTHER INFORMATION: R2PC12 VL FR1

<400> SEQUENCE: 38

Asp Ile Gln Met Thr Gln Ser Pro Ser Ser Leu Ser Ala Ser Val Gly
1               5                   10                  15
Asp Arg Val Thr Ile Thr Cys Lys Ala Ser
            20                  25

<210> SEQ ID NO 39
<211> LENGTH: 17
<212> TYPE: PRT
<213> ORGANISM: Artificial Sequence
<220> FEATURE:
<223> OTHER INFORMATION: R2PC12 VL FR2

<400> SEQUENCE: 39

Leu Asn Trp Tyr Gln Gln Lys Pro Gly Glu Ala Pro Lys Leu Leu Ile
1               5                   10                  15
Tyr

<210> SEQ ID NO 40
<211> LENGTH: 36
<212> TYPE: PRT
<213> ORGANISM: Artificial Sequence

<220> FEATURE:
<223> OTHER INFORMATION: R2PC12 VL FR3

<400> SEQUENCE: 40

Ile Leu Glu Thr Gly Val Pro Ser Arg Phe Ser Gly Ser Gly Ser Gly
1               5                   10                  15

Thr Asp Phe Thr Phe Thr Ile Ser Ser Leu Gln Pro Glu Asp Ile Ala
            20                  25                  30

Thr Tyr Tyr Cys
        35

<210> SEQ ID NO 41
<211> LENGTH: 10
<212> TYPE: PRT
<213> ORGANISM: Artificial Sequence
<220> FEATURE:
<223> OTHER INFORMATION: R2PC12 VL FR4

<400> SEQUENCE: 41

Phe Gly Gly Gly Thr Lys Leu Glu Ile Lys
1               5                   10

<210> SEQ ID NO 42
<211> LENGTH: 25
<212> TYPE: PRT
<213> ORGANISM: Artificial Sequence
<220> FEATURE:
<223> OTHER INFORMATION: R2PC28 VH FR1

<400> SEQUENCE: 42

Glu Val Gln Leu Val Glu Ser Gly Gly Ala Leu Val Gln Pro Gly Gly
1               5                   10                  15

Ser Leu Arg Leu Ser Cys Val Gly Ser
            20                  25

<210> SEQ ID NO 43
<211> LENGTH: 17
<212> TYPE: PRT
<213> ORGANISM: Artificial Sequence
<220> FEATURE:
<223> OTHER INFORMATION: R2PC28 VH FR2

<400> SEQUENCE: 43

Leu His Trp Val Arg Gln Ala Pro Gly Lys Gly Leu Glu Trp Leu Ala
1               5                   10                  15

Val

<210> SEQ ID NO 44
<211> LENGTH: 38
<212> TYPE: PRT
<213> ORGANISM: Artificial Sequence
<220> FEATURE:
<223> OTHER INFORMATION: R2PC28 VH FR3

<400> SEQUENCE: 44

Tyr Tyr Gly Asp Ser Val Lys Gly Arg Phe Thr Ile Ser Arg Asp Asn
1               5                   10                  15

Ser Lys Asn Thr Leu Tyr Leu Gln Met Asn Gly Leu Arg Ala Glu Asp
            20                  25                  30

Thr Ala Val Tyr Tyr Cys
        35

<210> SEQ ID NO 45

```
<211> LENGTH: 11
<212> TYPE: PRT
<213> ORGANISM: Artificial Sequence
<220> FEATURE:
<223> OTHER INFORMATION: R2PC28 VH FR4

<400> SEQUENCE: 45

Trp Gly Gln Gly Thr Met Val Thr Val Ser Ser
1               5                   10

<210> SEQ ID NO 46
<211> LENGTH: 26
<212> TYPE: PRT
<213> ORGANISM: Artificial Sequence
<220> FEATURE:
<223> OTHER INFORMATION: R2PC28 VL FR1

<400> SEQUENCE: 46

Glu Ile Val Leu Thr Gln Ser Pro Ala Thr Leu Ser Leu Ser Pro Gly
1               5                   10                  15

Glu Arg Ala Thr Leu Ser Cys Arg Ala Ser
            20                  25

<210> SEQ ID NO 47
<211> LENGTH: 17
<212> TYPE: PRT
<213> ORGANISM: Artificial Sequence
<220> FEATURE:
<223> OTHER INFORMATION: R2PC28 VL FR2

<400> SEQUENCE: 47

Leu Ala Trp Tyr Gln Gln Arg Pro Gly Gln Pro Pro Arg Leu Leu Ile
1               5                   10                  15

Tyr

<210> SEQ ID NO 48
<211> LENGTH: 36
<212> TYPE: PRT
<213> ORGANISM: Artificial Sequence
<220> FEATURE:
<223> OTHER INFORMATION: R2PC28 VL FR3

<400> SEQUENCE: 48

Asn Arg Ala Thr Gly Val Ala Ala Arg Phe Ser Gly Ser Gly Ser Gly
1               5                   10                  15

Thr Asp Phe Thr Leu Thr Ile Asp Ser Leu Glu Ala Glu Asp Ala Ala
            20                  25                  30

Thr Tyr Tyr Cys
        35

<210> SEQ ID NO 49
<211> LENGTH: 10
<212> TYPE: PRT
<213> ORGANISM: Artificial Sequence
<220> FEATURE:
<223> OTHER INFORMATION: R2PC28 VL FR4

<400> SEQUENCE: 49

Phe Gly Gln Gly Thr Lys Leu Glu Ile Lys
1               5                   10

<210> SEQ ID NO 50
<211> LENGTH: 25
<212> TYPE: PRT
<213> ORGANISM: Artificial Sequence
```

```
<220> FEATURE:
<223> OTHER INFORMATION: R2PC29 VH FR1

<400> SEQUENCE: 50

Gln Val Gln Leu Gln Gln Ser Gly Ala Glu Met Lys Lys Ser Gly Ser
1               5                   10                  15

Ser Val Lys Val Ser Cys Lys Ala Ser
            20                  25

<210> SEQ ID NO 51
<211> LENGTH: 17
<212> TYPE: PRT
<213> ORGANISM: Artificial Sequence
<220> FEATURE:
<223> OTHER INFORMATION: R2PC29 VH FR2

<400> SEQUENCE: 51

Ile Ser Trp Val Arg Gln Ala Pro Gly Gln Gly Leu Glu Trp Met Gly
1               5                   10                  15

Gly

<210> SEQ ID NO 52
<211> LENGTH: 38
<212> TYPE: PRT
<213> ORGANISM: Artificial Sequence
<220> FEATURE:
<223> OTHER INFORMATION: R2PC29 VH FR3

<400> SEQUENCE: 52

Asn Tyr Ala Gln Lys Phe Gln Gly Arg Val Thr Ile Thr Ala Asp Glu
1               5                   10                  15

Ser Thr Thr Thr Val Tyr Leu Gln Leu Thr Ser Leu Thr Pro Glu Asp
            20                  25                  30

Thr Ala Met Tyr Phe Cys
            35

<210> SEQ ID NO 53
<211> LENGTH: 11
<212> TYPE: PRT
<213> ORGANISM: Artificial Sequence
<220> FEATURE:
<223> OTHER INFORMATION: R2PC29 VH FR4

<400> SEQUENCE: 53

Trp Gly Gln Gly Thr Met Val Thr Val Ser Ser
1               5                   10

<210> SEQ ID NO 54
<211> LENGTH: 26
<212> TYPE: PRT
<213> ORGANISM: Artificial Sequence
<220> FEATURE:
<223> OTHER INFORMATION: R2PC29 VL FR1

<400> SEQUENCE: 54

Asp Ile Val Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 55
<211> LENGTH: 17
<212> TYPE: PRT
<213> ORGANISM: Artificial Sequence
```

<220> FEATURE:
<223> OTHER INFORMATION: R2PC29 VL FR2

<400> SEQUENCE: 55

Leu Asn Trp Tyr Gln Gln Lys Pro Gly Lys Ala Pro Asn Leu Leu Ile
1               5                   10                  15

Tyr

<210> SEQ ID NO 56
<211> LENGTH: 36
<212> TYPE: PRT
<213> ORGANISM: Artificial Sequence
<220> FEATURE:
<223> OTHER INFORMATION: R2PC29 VL FR3

<400> SEQUENCE: 56

Ser Leu Gln Ser Gly Val Pro Ser Arg Phe Arg Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 57
<211> LENGTH: 10
<212> TYPE: PRT
<213> ORGANISM: Artificial Sequence
<220> FEATURE:
<223> OTHER INFORMATION: R2PC29 VL FR4

<400> SEQUENCE: 57

Phe Gly Gln Gly Thr Lys Leu Glu Ile Lys
1               5                   10

<210> SEQ ID NO 58
<211> LENGTH: 25
<212> TYPE: PRT
<213> ORGANISM: Artificial Sequence
<220> FEATURE:
<223> OTHER INFORMATION: R2PC45 VH FR1

<400> SEQUENCE: 58

Gln Val Asn Leu Arg Glu Ser Gly Gly Gly Val Val Gln Pro Gly Arg
1               5                   10                  15

Ser Leu Arg Leu Ser Cys Ala Ala Ser
            20                  25

<210> SEQ ID NO 59
<211> LENGTH: 17
<212> TYPE: PRT
<213> ORGANISM: Artificial Sequence
<220> FEATURE:
<223> OTHER INFORMATION: R2PC45 VH FR2

<400> SEQUENCE: 59

Met His Trp Val Arg Gln Ala Pro Gly Lys Gly Leu Glu Trp Val Ala
1               5                   10                  15

Val

<210> SEQ ID NO 60
<211> LENGTH: 38
<212> TYPE: PRT
<213> ORGANISM: Artificial Sequence
<220> FEATURE:

<223> OTHER INFORMATION: R2PC45 VH FR3

<400> SEQUENCE: 60

Tyr Tyr Ala Asp Ser Val Lys Gly Arg Phe Thr Ile Ser Arg Asp Asn
1               5                   10                  15

Ser Lys Asn Thr Leu Tyr Leu Gln Met Asn Ser Leu Arg Ala Glu Asp
            20                  25                  30

Thr Ala Val Tyr Tyr Cys
        35

<210> SEQ ID NO 61
<211> LENGTH: 11
<212> TYPE: PRT
<213> ORGANISM: Artificial Sequence
<220> FEATURE:
<223> OTHER INFORMATION: R2PC45 VH FR4

<400> SEQUENCE: 61

Trp Gly Gln Gly Thr Met Val Thr Val Ser Ser
1               5                   10

<210> SEQ ID NO 62
<211> LENGTH: 26
<212> TYPE: PRT
<213> ORGANISM: Artificial Sequence
<220> FEATURE:
<223> OTHER INFORMATION: R2PC45 VL FR1

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 63
<211> LENGTH: 17
<212> TYPE: PRT
<213> ORGANISM: Artificial Sequence
<220> FEATURE:
<223> OTHER INFORMATION: R2PC45 VL FR2

<400> SEQUENCE: 63

Leu Asn Trp Tyr Gln Gln Lys Pro Gly Lys Ala Pro Lys Leu Leu Ile
1               5                   10                  15

Tyr

<210> SEQ ID NO 64
<211> LENGTH: 36
<212> TYPE: PRT
<213> ORGANISM: Artificial Sequence
<220> FEATURE:
<223> OTHER INFORMATION: R2PC45 VL FR3

<400> SEQUENCE: 64

Asn Leu Gln Ser Gly Val Pro Ser Arg Phe Ser Gly Ser Gly Ser Gly
1               5                   10                  15

Thr Asp Phe Thr Leu Thr Ile Asn Gly Leu Gln Pro Asp Asp Phe Ala
            20                  25                  30

Ile Tyr Phe Cys
        35

<210> SEQ ID NO 65
<211> LENGTH: 10

```
<212> TYPE: PRT
<213> ORGANISM: Artificial Sequence
<220> FEATURE:
<223> OTHER INFORMATION: R2PC45 VL FR4

<400> SEQUENCE: 65

Phe Gly Gln Gly Thr Lys Val Glu Ile Lys
1               5                   10

<210> SEQ ID NO 66
<211> LENGTH: 6
<212> TYPE: PRT
<213> ORGANISM: Homo sapiens

<400> SEQUENCE: 66

Asn Trp Glu Tyr Pro Ser
1               5

<210> SEQ ID NO 67
<211> LENGTH: 7
<212> TYPE: PRT
<213> ORGANISM: Homo sapiens

<400> SEQUENCE: 67

Thr Gln Ser Gly Ser Glu Met
1               5

<210> SEQ ID NO 68
<211> LENGTH: 6
<212> TYPE: PRT
<213> ORGANISM: Mus musculus

<400> SEQUENCE: 68

Thr Trp His Ser Pro Pro
1               5

<210> SEQ ID NO 69
<211> LENGTH: 7
<212> TYPE: PRT
<213> ORGANISM: Mus musculus

<400> SEQUENCE: 69

Pro Phe Pro Gly Thr Val Ala
1               5

<210> SEQ ID NO 70
<211> LENGTH: 59
<212> TYPE: DNA
<213> ORGANISM: Artificial Sequence
<220> FEATURE:
<223> OTHER INFORMATION: Anti-VEGFR2 shRNA sequence

<400> SEQUENCE: 70
ccggcgctga catgtacggt ctatgctcga gcatagaccg tacatgtcag cgttttttg      59

<210> SEQ ID NO 71
<211> LENGTH: 22
<212> TYPE: DNA
<213> ORGANISM: Artificial Sequence
<220> FEATURE:
<223> OTHER INFORMATION: VEGFR2-F primer

<400> SEQUENCE: 71
gaacatttgg gaaatctctt gc                                              22
```

<210> SEQ ID NO 72
<211> LENGTH: 23
<212> TYPE: DNA
<213> ORGANISM: Artificial Sequence
<220> FEATURE:
<223> OTHER INFORMATION: VEGFR2-R primer

<400> SEQUENCE: 72
cggaagaaca atgtagtctt tgc                                           23

<210> SEQ ID NO 73
<211> LENGTH: 9
<212> TYPE: PRT
<213> ORGANISM: Artificial Sequence
<220> FEATURE:
<223> OTHER INFORMATION: R2S12AF variable light chain CDR3

<400> SEQUENCE: 73

Gln Gln Leu Asp Asp Ile Pro Ile Thr
1               5

<210> SEQ ID NO 74
<211> LENGTH: 1356
<212> TYPE: PRT
<213> ORGANISM: Homo sapiens

<400> SEQUENCE: 74

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
                20                  25                  30

Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
        50                  55                  60

Asn Asn Gln Ser Gly Ser Glu Gln Arg Val Glu Val Thr Glu Cys Ser
65                  70                  75                  80

Asp Gly Leu Phe Cys Lys Thr Leu Thr Ile Pro Lys Val Ile Gly Asn
                85                  90                  95

Asp Thr Gly Ala Tyr Lys Cys Phe Tyr Arg Glu Thr Asp Leu Ala Ser
            100                 105                 110

Val Ile Tyr Val Tyr Val Gln Asp Tyr Arg Ser Pro Phe Ile Ala Ser
        115                 120                 125

Val Ser Asp Gln His Gly Val Val Tyr Ile Thr Glu Asn Lys Asn Lys
    130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
            180                 185                 190

Ser Tyr Ala Gly Met Val Phe Cys Glu Ala Lys Ile Asn Asp Glu Ser
        195                 200                 205

Tyr Gln Ser Ile Met Tyr Ile Val Val Val Gly Tyr Arg Ile Tyr
    210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

```
Asp Phe Asn Trp Glu Tyr Pro Ser Ser Lys His Gln His Lys Lys Leu
            260                 265                 270

Val Asn Arg Asp Leu Lys Thr Gln Ser Gly Ser Glu Met Lys Lys Phe
        275                 280                 285

Leu Ser Thr Leu Thr Ile Asp Gly Val Thr Arg Ser Asp Gln Gly Leu
    290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
            340                 345                 350

Lys Tyr Leu Gly Tyr Pro Pro Glu Ile Lys Trp Tyr Lys Asn Gly
        355                 360                 365

Ile Pro Leu Glu Ser Asn His Thr Ile Lys Ala Gly His Val Leu Thr
    370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
            420                 425                 430

Asp Ser Tyr Gln Tyr Gly Thr Thr Gln Thr Leu Thr Cys Thr Val Tyr
        435                 440                 445

Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Glu Asp Phe Gln Gly Gly Asn Lys
                485                 490                 495

Ile Glu Val Asn Lys Asn Gln Phe Ala Leu Ile Glu Gly Lys Asn Lys
            500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
    530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
            580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670
```

```
Leu Glu Asn Gln Thr Thr Ser Ile Gly Glu Ser Ile Glu Val Ser Cys
675                 680                 685

Thr Ala Ser Gly Asn Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Leu
    755                 760                 765

Val Gly Thr Ala Val Ile Ala Met Phe Phe Trp Leu Leu Leu Val Ile
770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
850                 855                 860

Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
            980                 985                 990

Glu Asp Leu Tyr Lys Asp Phe Leu Thr Leu Glu His Leu Ile Cys Tyr
        995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
```

```
                    1085                1090               1095

Phe Ser Leu Gly Ala Ser Pro Tyr Pro Gly Val Lys Ile Asp Glu
        1100                1105               1110

Glu Phe Cys Arg Arg Leu Lys Glu Gly Thr Arg Met Arg Ala Pro
        1115                1120               1125

Asp Tyr Thr Thr Pro Glu Met Tyr Gln Thr Met Leu Asp Cys Trp
        1130                1135               1140

His Gly Glu Pro Ser Gln Arg Pro Thr Phe Ser Glu Leu Val Glu
        1145                1150               1155

His Leu Gly Asn Leu Leu Gln Ala Asn Ala Gln Gln Asp Gly Lys
        1160                1165               1170

Asp Tyr Ile Val Leu Pro Ile Ser Glu Thr Leu Ser Met Glu Glu
        1175                1180               1185

Asp Ser Gly Leu Ser Leu Pro Thr Ser Pro Val Ser Cys Met Glu
        1190                1195               1200

Glu Glu Glu Val Cys Asp Pro Lys Phe His Tyr Asp Asn Thr Ala
        1205                1210               1215

Gly Ile Ser Gln Tyr Leu Gln Asn Ser Lys Arg Lys Ser Arg Pro
        1220                1225               1230

Val Ser Val Lys Thr Phe Glu Asp Ile Pro Leu Glu Glu Pro Glu
        1235                1240               1245

Val Lys Val Ile Pro Asp Asp Asn Gln Thr Asp Ser Gly Met Val
        1250                1255               1260

Leu Ala Ser Glu Glu Leu Lys Thr Leu Glu Asp Arg Thr Lys Leu
        1265                1270               1275

Ser Pro Ser Phe Gly Gly Met Val Pro Ser Lys Ser Arg Glu Ser
        1280                1285               1290

Val Ala Ser Glu Gly Ser Asn Gln Thr Ser Gly Tyr Gln Ser Gly
        1295                1300               1305

Tyr His Ser Asp Asp Thr Asp Thr Thr Val Tyr Ser Ser Glu Glu
        1310                1315               1320

Ala Glu Leu Leu Lys Leu Ile Glu Ile Gly Val Gln Thr Gly Ser
        1325                1330               1335

Thr Ala Gln Ile Leu Gln Pro Asp Ser Gly Thr Thr Leu Ser Ser
        1340                1345               1350

Pro Pro Val
        1355

<210> SEQ ID NO 75
<211> LENGTH: 5
<212> TYPE: PRT
<213> ORGANISM: Homo sapiens

<400> SEQUENCE: 75

Gly Leu Met Thr Lys
1               5

<210> SEQ ID NO 76
<211> LENGTH: 117
<212> TYPE: PRT
<213> ORGANISM: Artificial Sequence
<220> FEATURE:
<223> OTHER INFORMATION: VH region of R2S12 or R2S12-AF

<400> SEQUENCE: 76

Gln Val Asn Leu Arg Glu Ser Gly Gly Gly Leu Val Lys Pro Gly Gly
1               5                   10                  15
```

Ser Leu Arg Leu Ser Cys Ala Ala Ser Gly Phe Thr Phe Gly Ser Tyr
            20                  25                  30

Thr Met Asn Trp Val Arg Gln Ala Pro Gly Lys Gly Leu Glu Trp Val
        35                  40                  45

Ala Ser Ile Thr Ser Gly Ser Ser Tyr Ile Phe Tyr Thr Asp Ser Val
50                  55                  60

Lys Gly Arg Phe Thr Ile Ser Arg Asp Asn Ser Arg Ser Ser Leu Phe
65                  70                  75                  80

Leu Gln Met Asn Ser Leu Arg Ala Glu Asp Thr Ala Ile Tyr Tyr Cys
                85                  90                  95

Ala Arg Gly Ser Ala Ser Ala Phe Asp Ile Trp Gly Gln Gly Thr Met
            100                 105                 110

Val Thr Val Ser Ser
            115

<210> SEQ ID NO 77
<211> LENGTH: 107
<212> TYPE: PRT
<213> ORGANISM: Artificial Sequence
<220> FEATURE:
<223> OTHER INFORMATION: VL region of R2S12

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Asp Ile Ile Asn Tyr
            20                  25                  30

Leu Asn Trp Tyr Gln Gln Lys Pro Gly Glu Ala Pro Lys Leu Leu Ile
        35                  40                  45

Tyr Asp Ala Ser Ile Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Ile Leu Pro Leu
                85                  90                  95

Thr Phe Gly Gly Gly Thr Lys Leu Glu Ile Lys
            100                 105

<210> SEQ ID NO 78
<211> LENGTH: 107
<212> TYPE: PRT
<213> ORGANISM: Artificial Sequence
<220> FEATURE:
<223> OTHER INFORMATION: VL region of R2S12AF

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Asp Ile Ile Asn Tyr
            20                  25                  30

Leu Asn Trp Tyr Gln Gln Lys Pro Gly Glu Ala Pro Lys Leu Leu Ile
        35                  40                  45

Tyr Asp Ala Ser Ile Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Leu Asp Asp Ile Pro Ile

```
                    85                  90                  95

Thr Phe Gly Gly Gly Thr Lys Leu Glu Ile Lys
                100                 105

<210> SEQ ID NO 79
<211> LENGTH: 330
<212> TYPE: PRT
<213> ORGANISM: Homo sapiens

<400> SEQUENCE: 79

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 80
<211> LENGTH: 1340
```

<212> TYPE: PRT
<213> ORGANISM: Mus musculus

<400> SEQUENCE: 80

```
Met Glu Ser Lys Ala Leu Leu Ala Val Ala Leu Trp Phe Cys Val Glu
1               5                   10                  15

Thr Arg Ala Ala Ser Val Gly Leu Pro Gly Asp Phe Leu His Pro Pro
            20                  25                  30

Lys Leu Ser Thr Gln Lys Asp Ile Leu Thr Ile Leu Ala Asn Thr Thr
        35                  40                  45

Leu Gln Ile Thr Cys Arg Gly Gln Arg Asp Leu Asp Trp Leu Trp Pro
    50                  55                  60

Asn Ala Gln Arg Asp Ser Glu Glu Arg Val Leu Val Thr Glu Cys Gly
65                  70                  75                  80

Gly Gly Asp Ser Ile Phe Cys Lys Thr Leu Thr Ile Pro Arg Val Val
                85                  90                  95

Gly Asn Asp Thr Gly Ala Tyr Lys Cys Ser Tyr Arg Asp Val Asp Ile
            100                 105                 110

Ala Ser Thr Val Tyr Val Tyr Val Arg Asp Tyr Arg Ser Pro Phe Ile
        115                 120                 125

Ala Ser Val Ser Asp Gln His Gly Ile Val Tyr Ile Thr Glu Asn Lys
    130                 135                 140

Asn Lys Thr Val Val Ile Pro Cys Arg Gly Ser Ile Ser Asn Leu Asn
145                 150                 155                 160

Val Ser Leu Cys Ala Arg Tyr Pro Glu Lys Arg Phe Val Pro Asp Gly
                165                 170                 175

Asn Arg Ile Ser Trp Asp Ser Glu Ile Gly Phe Thr Leu Pro Ser Tyr
            180                 185                 190

Met Ile Ser Tyr Ala Gly Met Val Phe Cys Glu Ala Lys Ile Asn Asp
        195                 200                 205

Glu Thr Tyr Gln Ser Ile Met Tyr Ile Val Val Val Gly Val Ile
    210                 215                 220

Leu Ser Pro Pro His Glu Ile Glu Leu Ser Ala Gly Glu Lys Leu Val
225                 230                 235                 240

Leu Asn Cys Thr Ala Arg Thr Glu Leu Asn Val Gly Leu Asp Phe Thr
                245                 250                 255

Trp His Ser Pro Pro Ser Lys Ser His His Lys Lys Ile Val Asn Arg
            260                 265                 270

Asp Val Lys Pro Phe Pro Gly Thr Val Ala Lys Met Phe Leu Ser Thr
        275                 280                 285

Leu Thr Ile Glu Ser Val Thr Lys Ser Asp Gln Gly Glu Tyr Thr Cys
    290                 295                 300

Val Ala Ser Ser Gly Arg Met Ile Lys Arg Asn Arg Thr Phe Val Arg
305                 310                 315                 320

Val His Thr Lys Pro Phe Ile Ala Phe Gly Ser Gly Met Lys Ser Leu
                325                 330                 335

Val Glu Ala Thr Val Gly Ser Gln Val Arg Ile Pro Val Lys Tyr Leu
            340                 345                 350

Ser Tyr Pro Ala Pro Asp Ile Lys Trp Tyr Arg Asn Gly Arg Pro Ile
        355                 360                 365

Glu Ser Asn Tyr Thr Met Ile Val Gly Asp Glu Leu Thr Ile Met Glu
    370                 375                 380

Val Thr Glu Arg Asp Ala Gly Asn Tyr Thr Val Ile Leu Thr Asn Pro
385                 390                 395                 400
```

-continued

```
Ile Ser Met Glu Lys Gln Ser His Met Val Ser Leu Val Val Asn Val
                405                 410                 415
Pro Pro Gln Ile Gly Glu Lys Ala Leu Ile Ser Pro Met Asp Ser Tyr
                420                 425                 430
Gln Tyr Gly Thr Met Gln Thr Leu Thr Cys Thr Val Tyr Ala Asn Pro
                435                 440                 445
Pro Leu His His Ile Gln Trp Tyr Trp Gln Leu Glu Glu Ala Cys Ser
                450                 455                 460
Tyr Arg Pro Gly Gln Thr Ser Pro Tyr Ala Cys Lys Glu Trp Arg His
465                 470                 475                 480
Val Glu Asp Phe Gln Gly Gly Asn Lys Ile Glu Val Thr Lys Asn Gln
                485                 490                 495
Tyr Ala Leu Ile Glu Gly Lys Asn Lys Thr Val Ser Thr Leu Val Ile
                500                 505                 510
Gln Ala Ala Asn Val Ser Ala Leu Tyr Lys Cys Glu Ala Ile Asn Lys
                515                 520                 525
Ala Gly Arg Gly Glu Arg Val Ile Ser Phe His Val Ile Arg Gly Pro
                530                 535                 540
Glu Ile Thr Val Gln Pro Ala Ala Gln Pro Thr Glu Gln Glu Ser Val
545                 550                 555                 560
Ser Leu Leu Cys Thr Ala Asp Arg Asn Thr Phe Glu Asn Leu Thr Trp
                565                 570                 575
Tyr Lys Leu Gly Ser Gln Ala Thr Ser Val His Met Gly Glu Ser Leu
                580                 585                 590
Thr Pro Val Cys Lys Asn Leu Asp Ala Leu Trp Lys Leu Asn Gly Thr
                595                 600                 605
Met Phe Ser Asn Ser Thr Asn Asp Ile Leu Ile Val Ala Phe Gln Asn
                610                 615                 620
Ala Ser Leu Gln Asp Gln Gly Asp Tyr Val Cys Ser Ala Gln Asp Lys
625                 630                 635                 640
Lys Thr Lys Lys Arg His Cys Leu Val Lys Gln Leu Ile Ile Leu Glu
                645                 650                 655
Arg Met Ala Pro Met Ile Thr Gly Asn Leu Glu Asn Gln Thr Thr Thr
                660                 665                 670
Ile Gly Glu Thr Ile Glu Val Thr Cys Pro Ala Ser Gly Asn Pro Thr
                675                 680                 685
Pro His Ile Thr Trp Phe Lys Asp Asn Glu Thr Leu Val Glu Asp Ser
                690                 695                 700
Gly Ile Val Leu Arg Asp Gly Asn Arg Asn Leu Thr Ile Arg Arg Val
705                 710                 715                 720
Arg Lys Glu Asp Gly Gly Leu Tyr Thr Cys Gln Ala Cys Asn Val Leu
                725                 730                 735
Gly Cys Ala Arg Ala Glu Thr Leu Phe Ile Ile Glu Gly Ala Gln Glu
                740                 745                 750
Lys Thr Asn Leu Glu Val Ile Ile Leu Val Gly Thr Ala Val Ile Ala
                755                 760                 765
Met Phe Phe Trp Leu Leu Leu Val Ile Val Leu Arg Thr Val Lys Arg
                770                 775                 780
Ala Asn Glu Gly Glu Leu Lys Thr Gly Tyr Leu Ser Ile Val Met Asp
785                 790                 795                 800
Pro Asp Glu Leu Pro Leu Asp Glu Arg Cys Glu Arg Leu Pro Tyr Asp
                805                 810                 815
```

```
Ala Ser Lys Trp Glu Phe Pro Arg Asp Arg Leu Lys Leu Gly Lys Pro
            820                 825                 830

Leu Gly Arg Gly Ala Phe Gly Gln Val Ile Glu Ala Asp Ala Phe Gly
        835                 840                 845

Ile Asp Lys Thr Ala Thr Cys Lys Thr Val Ala Val Lys Met Leu Lys
    850                 855                 860

Glu Gly Ala Thr His Ser Glu His Arg Ala Leu Met Ser Glu Leu Lys
865                 870                 875                 880

Ile Leu Ile His Ile Gly His His Leu Asn Val Val Asn Leu Leu Gly
                885                 890                 895

Ala Cys Thr Lys Pro Gly Gly Pro Leu Met Val Ile Val Glu Phe Cys
        900                 905                 910

Lys Phe Gly Asn Leu Ser Thr Tyr Leu Arg Gly Lys Arg Asn Glu Phe
    915                 920                 925

Val Pro Tyr Lys Ser Lys Gly Ala Arg Phe Arg Gln Gly Lys Asp Tyr
        930                 935                 940

Val Gly Glu Leu Ser Val Asp Leu Lys Arg Arg Leu Asp Ser Ile Thr
945                 950                 955                 960

Ser Ser Gln Ser Ser Ala Ser Ser Gly Phe Val Glu Glu Lys Ser Leu
                965                 970                 975

Ser Asp Val Glu Glu Glu Glu Ala Ser Glu Glu Leu Tyr Lys Asp Phe
        980                 985                 990

Leu Thr Leu Glu His Leu Ile Cys Tyr Ser Phe Gln Val Ala Lys Gly
            995                 1000                1005

Met Glu Phe Leu Ala Ser Arg Lys Cys Ile His Arg Asp Leu Ala
    1010                1015                1020

Ala Arg Asn Ile Leu Leu Ser Glu Lys Asn Val Val Lys Ile Cys
    1025                1030                1035

Asp Phe Gly Leu Ala Arg Asp Ile Tyr Lys Asp Pro Asp Tyr Val
    1040                1045                1050

Arg Lys Gly Asp Ala Arg Leu Pro Leu Lys Trp Met Ala Pro Glu
    1055                1060                1065

Thr Ile Phe Asp Arg Val Tyr Thr Ile Gln Ser Asp Val Trp Ser
    1070                1075                1080

Phe Gly Val Leu Leu Trp Glu Ile Phe Ser Leu Gly Ala Ser Pro
    1085                1090                1095

Tyr Pro Gly Val Lys Ile Asp Glu Glu Phe Cys Arg Arg Leu Lys
    1100                1105                1110

Glu Gly Thr Arg Met Arg Ala Pro Asp Tyr Thr Thr Pro Glu Met
    1115                1120                1125

Tyr Gln Thr Met Leu Asp Cys Trp His Glu Asp Pro Asn Gln Arg
    1130                1135                1140

Pro Ser Phe Ser Glu Leu Val Glu His Leu Gly Asn Leu Leu Gln
    1145                1150                1155

Ala Asn Ala Gln Gln Asp Gly Lys Asp Tyr Ile Val Leu Pro Met
    1160                1165                1170

Ser Glu Thr Leu Ser Met Glu Glu Asp Ser Gly Leu Ser Leu Pro
    1175                1180                1185

Thr Ser Pro Val Ser Cys Met Glu Glu Glu Glu Val Cys Asp Pro
    1190                1195                1200

Lys Phe His Tyr Asp Asn Thr Ala Gly Ile Ser His Tyr Leu Gln
    1205                1210                1215
```

```
Asn Ser Lys Arg Lys Ser Arg Pro Val Ser Val Lys Thr Phe Glu
    1220                1225                1230

Asp Ile Pro Leu Glu Glu Pro Glu Val Lys Val Ile Pro Asp Asp
    1235                1240                1245

Ser Gln Thr Asp Ser Gly Met Val Leu Ala Ser Glu Glu Leu Lys
    1250                1255                1260

Thr Leu Glu Asp Arg Asn Lys Leu Ser Pro Ser Phe Gly Gly Met
    1265                1270                1275

Met Pro Ser Lys Ser Arg Glu Ser Val Ala Ser Glu Gly Ser Asn
    1280                1285                1290

Gln Thr Ser Gly Tyr Gln Ser Gly Tyr His Ser Asp Asp Thr Asp
    1295                1300                1305

Thr Thr Val Tyr Ser Ser Asp Glu Ala Gly Leu Leu Lys Met Val
    1310                1315                1320

Asp Ala Ala Val His Ala Asp Ser Gly Thr Thr Leu Arg Ser Pro
    1325                1330                1335

Pro Val
    1340
```